United States Patent
Pantano et al.

(10) Patent No.: US 6,487,326 B1
(45) Date of Patent: Nov. 26, 2002

(54) THIN FILM FIBER OPTIC ELECTRODE SENSOR ARRAY AND APPARATUS

(75) Inventors: Paul Pantano, Plano; Eunsook S. Jin; Samina S. Khan, both of Richardson; Harold W. Stokes, Jr., Mesquite, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/450,156

(22) Filed: Nov. 29, 1999

(51) Int. Cl.[7] ................................. G02B 6/10
(52) U.S. Cl. .................. 385/12; 385/147; 385/115; 385/120; 385/38; 385/116; 422/82.07; 436/84; 436/172
(58) Field of Search ............... 422/82.07; 436/172, 436/164; 385/12, 115, 120, 38, 116, 147

(56) References Cited

U.S. PATENT DOCUMENTS

| | | | |
|---|---|---|---|
| 4,280,815 A | 7/1981 | Oberhardt, et al. | 23/230 B |
| 4,380,074 A | 4/1983 | Walsh | 372/43 |
| 4,419,696 A | 12/1983 | Hamano et al. | 358/294 |
| 4,902,088 A | 2/1990 | Jain et al. | 350/96.14 |
| 5,007,695 A | 4/1991 | Chang | 350/96.14 |
| 5,047,627 A * | 9/1991 | Yim et al. | |
| 5,098,659 A * | 3/1992 | Yim et al. | |
| 5,127,077 A * | 6/1992 | Iyer et al. | |
| 5,131,065 A | 7/1992 | Briggs et al. | 385/120 |
| 5,202,941 A | 4/1993 | Granestrand | 385/41 |
| 5,506,721 A | 4/1996 | Hikami et al. | 359/285 |
| 5,646,863 A | 7/1997 | Morton | 364/496 |
| 5,676,820 A | 10/1997 | Wang et al. | 205/777.5 |
| 5,696,863 A * | 12/1997 | Kleinerman | |
| 5,729,641 A | 3/1998 | Chandonnet et al. | 385/2 |

FOREIGN PATENT DOCUMENTS

| | | | | |
|---|---|---|---|---|
| FI | WO 98/36266 | 8/1998 | | G01N/21/66 |
| WO | WO 99/58962 | 11/1999 | | G01N/21/66 |

OTHER PUBLICATIONS

"Analytical Applications of Optical Imaging Fibers," Paul Pantano, David R. Walt, Analytical Chemistry, Aug. 1, 1995, pp. 481A–487A.

* cited by examiner

Primary Examiner—Hung N. Ngo
(74) Attorney, Agent, or Firm—Edwin S. Flores; Sanford E. Warren, Jr.; Gardere Wynne Sewell LLP

(57) ABSTRACT

An apparatus and method is disclosed for detecting an analyte using a fiber optic electrochemical sensor that includes a fiber optic layer, an electrically conductive translucent metallic layer and a light energy absorbing dye layer.

22 Claims, 10 Drawing Sheets

THIN FILM FIBER OPTIC ELECTRODE SENSOR ARRAY AND APPARATUS

The Government may own certain rights in this invention pursuant to any federal grants?

TECHNICAL FIELD OF THE INVENTION

The invention relates to combined optical and electrochemical detection, and more particularly, to an apparatus and method for use in the performance of such studies.

BACKGROUND OF THE INVENTION

Without limiting the scope of the invention, its background is described in connection with a combined electrochemical and optical apparatus for luminescence imaging of microenvironments and methods that may be used in the performance of such imaging.

Fluorescence imaging is one of the most valuable methods for analyzing microenvironments, particularly cellular microenvironments, and can be expected to find broader applicability as the rapidly growing computer and video industries provide new tools/hardware for fluorescence imaging. Although promising in theory, fluorescence microscopy is limited by the number of analytes that are amenable to fluorescent detection schemes. While it is straightforward to image analytes with native fluorescence, analytes labeled with a fluorophore, or analytes that can interact with a fluorescent indicator (e.g., $H^+$, $Ca^{2+}$, $O_2$), imaging other species such as electroactive analytes is problematic. For example, a major intracellular electroactive analyte of particular importance in understanding cellular metabolism, hydrogen peroxide ($H_2O_2$) is presently unamenable to continuous fluorescent analysis on a cellular resolution level.

The motivation for imaging hydrogen peroxide and other reactive oxygen species (ROS) in biological cells and tissue stems from their role in oxidative stress and oxidative burst events. Unfortunately, the in situ monitoring of ROS dynamics on the cellular level is limited by existing technology. Currently, the most common microscopic method for imaging hydrogen peroxide involves loading cells with dichlorofluorescin and quantitating the hydrogen peroxide by following the oxidation of dichlorofluorescin by hydrogen peroxide to produce fluorescent dichlorofluorescein. This technique can be used for detecting ROS liberated in or diffusing in the cytosol of the cell but it is not a direct reporter for ROS generated at the plasma membrane and/or released to the exterior of the cell. Hydrogen peroxide fiber-optic sensors or biosensors that are suitable for single cell analysis by virtue of the ability to acquire a continuous real time measurement with (sub)micrometer spatial resolution have not been demonstrated.

Nicotinamide adenine dinucleotide in its reduced form (NADH), is a biologically important coenzyme that is both fluorescent and electroactive. The quantitation of this molecule is of great interest in chemistry, biology, and medicine. For example, in addition to its use as a metabolic activity marker, NADH is an ideal biosensor reagent since it can modulate the activity of over 200 different dehydrogenases [Pantano, P. & Kuhr, W. G. (1995) *Electroanalysis* 7, 405–416]. Unfortunately, both the NADH fluorescence and electrochemical measurements are difficult to perform. For the NADH fluorescence measurement, in addition to its low quantum yield, there is significant biological (auto) fluorescence in the same spectral region as the NADH emission. Furthermore, the throughput of borosilicate glass and silica-based optical fibers is attenuated greatly in the ultraviolet spectral region where the NADH excitation wavelength lies (i.e., 340 nm). Finally, improving a CCD camera's 400–500 nm quantum efficiency (the NADH emission spectral region) by employing back-thinned chips is prohibitively expensive. Also, existing electrochemical fiber-optic NADH-biosensors lack the resolution required for imaging purposes.

What is needed is an apparatus and system that readily permits concurrent luminescence imaging and electrochemical sensing of important analytes with a microscopic level of resolution.

SUMMARY OF THE INVENTION

The present invention is directed to apparatus and methodology for concurrent fluorescence imaging and chemical sensing of an electroactive analyte through a fiber optic electrode with resolution on the microscopic level.

The fabrication and characterization of imaging fiber electrodes (IFEs) is presented, and the use of an electrochemically-modulated, fluorescence-based, imaging-fiber electrode chemical sensor (IFECS) is demonstrated.

In one embodiment, the invention provides a fiber optic electrochemical sensor for detecting an analyte including a fiber optic layer, a electrically conductive translucent metallic layer, and a light energy absorbing dye layer. The fiber optic layer of the fiber optic electrochemical sensor may be a fiber optic bundle that includes one or more of individual optic fibers, wherein each individual optic fiber has a diameter of less than 20 micrometers. In one embodiment, the fiber optic electrochemical sensor includes a fiber optic bundle with individual optic fibers, wherein each individual optic fiber has a diameter of less than 10 micrometers and wherein the bundle has a diameter of less than 2 millimeters. The sensor also has an electrically conductive translucent metallic layer, and a light energy absorbing dye layer wherein the fiber optic electrochemical sensor is capable of electrochemical regeneration. Due to its microscopic resolution capabilities, the apparatus and method of the present invention is particularly applicable to studies of cells and tissues, however, the scope of the invention is not limited to biological microenvironments but rather is applicable to any microenvironment in which fine spatial resolution of imaging concurrent with chemical sensing is needed.

In alternate embodiments, the electrically conductive translucent metallic layer of the fiber optic electrochemical sensor is between 10 and 100 nm thick. The metallic layer may be of any electrically conductive metal or metal oxide that may be applied in a translucent layer wherein "translucent", used interchangably herein with "transparent", means susceptible to the through-passage of light energy. In examples provided herein, the fiber optic electrochemical sensor electrically conductive translucent metallic layer is a sputter-coated 20–23 nm layer of gold.

In alternate embodiments, the light energy absorbing dye layer of the fiber optic electrochemical sensor is selected from the group consisting of, e.g. fluorochromes, fluorescent enzyme conjugates, fluorescent substrates and chromophores. In one example, the analyte to be detected is a cellular reactive oxygen species and the light energy absorbing dye layer includes a rhodamine dye.

In another example the analyte to be detected is cellular NADH and the light energy absorbing dye layer includes a ruthenium containing luminophore.

In another embodiment of an imaging system according to the present invention, a fluorescence based imaging fiber electrode chemical sensor system includes a fiber optic electrochemical sensor, a potentiomer or equivalent means for measuring ion flux, a microscope including a light source and an objective lens. The objective lens communicates light from the source to the fiber optic electrochemical sensor and receives light returning from the sensor and provides a means for recording light returning from the sensor though the objective. Potentially useful recording devices include CCD cameras, linear arrays and xy active matrix detectors.

The invention provides in one embodiment a method for preparing a imaging fiber electrode including the steps of; polishing a face of the fiber optic bundle, silanizing the face using a mercapto-trimethyoxysilane, and sputter coating the silanized face to deposit a 10–30 nm thick semi-transparent metal layer.

In another embodiment, a method for preparing a imaging fiber chemical sensor is provided including the steps of; obtaining a fiber optic electrode having a 15–30 nm gold film on a distal end and an electrically conductive aspect leading from the distal end through a lateral dimension of the fiber optic electrode, coating the fiber optic electrode with an ion-exchange polymer and applying a luminescent reporter group.

In one example of an ion-exchange polymer according to the present invention poly(tetrafluorethylene)polymers having characteristics of NAFION polymers have been found suitable.

In one embodiment, the invention provides a method of constructing and using electrochemically-modulated, fluorescence-based, imaging-fiber electrode chemical sensors (IFECS). An imaging fiber distal tip is coating with a semi-transparent metal layer to create an IFE. In an alternate embodiment the imaging fiber is sputter coated with a semi-transparent layer of gold although alternate coating methods with alternate metallic compounds and metal oxides may be applicable.

By "semi-transparent" or "translucent" according to the present invention, is meant a layer of gold sufficiently thin for light to be transmitted through it and yet thick enough to serve as an electrode. The term "gold" as used in the present invention includes gold and any alloy containing gold. A range of metal thickness of 10 to 100 nm may be expected to perform these dual roles under appropriate circumstances. A light energy absorbing dye such as a fluorescent redox dye is immobilized across the IFE face to create an IFECS. Alternate light energy absorbing dyes are known in the art and many are commercially available. Potentially applicable analyte responsive or reporter dyes may include either, or a mixture of, light emitting and light absorbing dyes or may include other materials such as enzymes, or antibodies, or chemical compounds. Potentially applicable luminescent reporters in addition to the specific examples of RBITC, NADH and tris(2,2'-bipyridyl)ruthenium provided herein may include for example such fluorochromes as: nile blue A, rhodamine 123, rubrene, rhodanile blue, eosin, TRITC-amine, quinine, fluorescein W, acridine yellow, lissamine rhodamine B sulfonyl chloride, erythroscein, Texas Red, phycoerythrin, flavin adenine dinucleotide (FAD), carboxy seminaphthorhodafluor, and naphthofluorescein. Fluorescent enzyme conjugates may be employed in some circumstances in addition to substrates such as for example: fluorescein mono-B-D-galacto-pyranoside, resorufin, B-d-glucuronide, 8-acetoxypyrene 1,3,6-trisulfonic acid trisodium salt, Coenzyme A (1-pyrene butanoic acid)ester, Fluo-3, and Quin-2. Potentially applicable chromophores include for some examples not intended to be limiting: iron-salicylate complex, Indamine dye, Hopkins-Cole dye, quinone-imine dye, $Fe(SCN)^{+2}$, Malachite Green, cresol red, diphenylcarbazone disulphonic acid, chrome bordeaux B, calmagite and ninhydrin dye. Applicable analyte responsive dyes may include either, or a mixture of, light emitting and light absorbing dyes or may include other materials such as enzymes, or antibodies, or chemical compounds. The reporter dyes may further include pairs of donor and acceptor molecules such as those known in the art to participate in fluorescence resonance energy transfer (FRET) in which excitation between two dye molecules is transferred from a donor molecule to an acceptor molecule without emission of a photon. Known examples of FRET pairs include Fluorescein/Tetramethylrhodamine, IAEDANS/Fluorescein, EDANS/DABCYL, Fluorescein/Fluorescein, BODIPY FL/BODIPY FL and Fluorescein/QSY-7 dye.

An electroactive analyte is imaged by monitoring the change in the immobilized redox dye's fluorescence following its homogeneous electron transfer reaction with an electroactive analyte. Fluorescence images were collected through the IFECS and detected by an imaging system such as for one example an epi-fluorescence microscope/CCD imaging system. Instead of using a CCD camera, other sensitive detectors such as for example linear array detectors or XY matrix photodetectors may be included in the imaging system. Cyclic voltammetry and fluorescence microscopy may be utilized to characterize the electrochemical and fluorescence properties of IFECSs.

In one embodiment of the present invention, reversible voltammetry was observed for the redox couple at IFEs permitting the sensor to be recharged and used for multiple measurements. In on example, IFECSs using RBITC as the fluorescent redox dye and NAFION as the immobilization polymer were fabricated to detect hydrogen peroxide. The IFECS's RBITC-fluorescence was decreased by ~27% upon exposure to 0.25 mM hydrogen peroxide and ~95% of the original fluorescence was observed following the electrochemical regeneration of the NAFION-immobilized RBITC. These IFECSs provide for remote fluorescence imaging of an electroactive analyte, which may be performed through the actual fiber-optic electrode itself and have the capacity to regenerate.

The invention provides a dual system that includes a potentiostat/electrochemistry system together with features of a combined imaging and chemical sensing approach. The combined imaging and chemical sensing (CICS) approach, permits viewing a sample and measuring surface chemical concentrations using an optical imaging fiber [Bronk, K. S., Michael, K. L., Pantano, P., Walt, D. R. (1995) *Anal Chem* 67:2750; Pantano, P., Walt, D. R. (1995) *Anal Chem* 67:481A; and Panova, A. A., Pantano, P., Walt, D. R. (1997) *Anal Chem* 69:1635]. According to the CICS approach to imaging, a high resolution imaging fiber may include thousands of individual optical fibers in a diameter range measured in $\mu m$ melted and drawn together such that an image can be carried and maintained in a coherent manner from one end to the other. As an example a 350-micrometer-diameter distal fiber surface, containing ~6000 optical sensors of ~3 micrometer diameter, is coated with a uniform, planar sensing layer that can measure chemical concentrations with spatial accuracy, yet is thin enough so that it does not compromise the fiber's imaging capabilities. By combining the distinct optical pathways of the imaging fiber with the spatial discrimination of a charge coupled device (CCD) camera, visual and fluorescence measurements can be obtained with 4-micrometer spatial resolution over thousands of square micrometers using a CICS approach. In the present invention, the concept of imaging fiber electrodes (IFE) is united with the CICS approach. The present inventors have developed a novel thin film fiber optic electrode sensor array and apparatus that permits both electrochemical and luminescence imaging through the actual sensor itself.

In one embodiment, the present invention provides a new apparatus and method for remote hydrogen peroxide imaging which unites the fabrication of imaging fiber electrodes with the combined imaging and chemical sensing approach. The present combined devices are termed herein "imaging fiber electrode chemical sensors (IFECSs)." In brief, an imaging fiber's distal tip is metalized to serve as an electrode (i.e., an IFE) before a light energy absorbing dye such as a fluorescent redox dye is immobilized across the IFE's distal face. Finally, in the case of a fluorescent redox dye, the redox state of the bound dye (and its initial fluorescence) is regenerated by application of a suitable potential across the IFE surface. While fluorescence and electrochemistry (i.e., electrodes and optical fibers) have been united previously, the present IFECSs permit remote fluorescence imaging to be performed through the actual fiber-optic electrode itself.

In one embodiment of the present invention there is provided a new technique for remote NADH imaging wherein combined imaging and chemical sensing of $Ru(bpy)_3^{2+}$-Electrogenerated Chemiluminescence is achieved. This has been accomplished by fabricating imaging fiber electrode (IFE) sensors. In one example, an imaging fiber's distal tip is metalized to serve as an electrode (i.e., an IFE). The IFE is coated with a thin, planar layer of NAFION doped with $Ru(bpy)_3^{2+}$ to produce an IFE Sensor. An electrical contact is made to the metal layer such that $Ru(bpy)_3^{2+}$ can be oxidized to $Ru(bpy)_3^{3+}$ and electrochemically regenerated following the application of an appropriate potential. Following the diffusion of NADH into the IFE sensing layer, the Electrogenerated Chemiluminescence emission is captured and analyte concentrations quantitated using a CCD-based imaging system.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used throughout the present specification the following abbreviations are used:

$H_2O_2$—Hydrogen peroxide

IFCP—Imaging fiber chemical probe

IFECS—Imaging fiber electrode chemical sensor

MPS—(3-mercaptopropyl)-trimethoxysilane

NADH—b-nicotinamide adenine dinucleotide, reduced form

NAFION—poly(tetrafluoroethylene)polymer that contains small proportions of sulfonic ionic functional groups invented by and registered trademark of DuPont RBITC—Rhodamine B isothiocyanate ROI—region of interest ROS—reactive oxygen species $Ru(bpy)_3^{2+}$—tris(2,2'-bipyridyl)ruthenium(II) chloride hexahydrate TEA—triethylamine As used herein a "luminophore" is a compound that is chemiluminescent or fluorescent.

The following examples of alternate embodiments of Thin Fiber Optic Electrode Sensor Arrays are include for the sake of completeness of disclosure and to illustrate the methods of making the compositions and composites of the present invention as well as to present certain characteristics of the compositions. In no way are these examples intended to limit the scope or teaching of this disclosure.

In one example an electrochemically-modulated chemiluminescence based imaging fiber chemical sensor is provided. Another example provides a electrochemically-modulated fluorescence based imaging fiber chemical sensor.

Figure 1A:
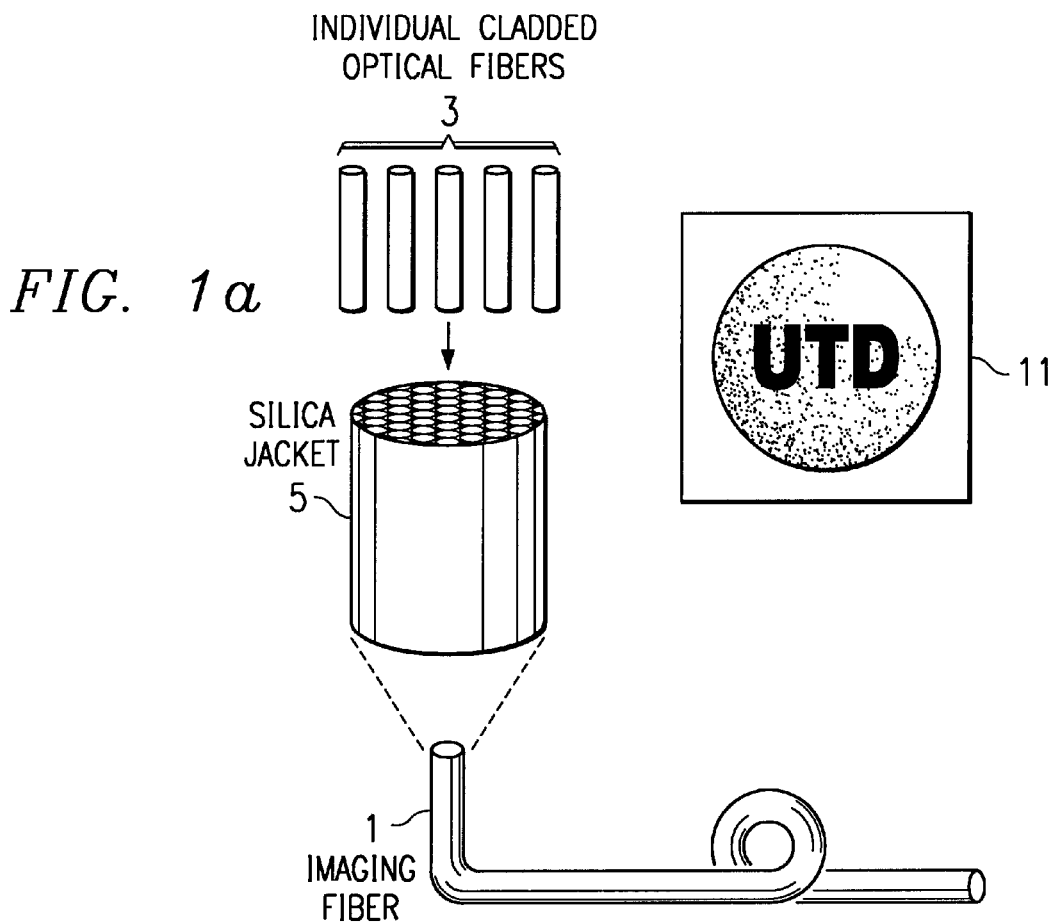
FIG. 1a: Schematic diagram of one embodiment of a coherent imaging fiber comprising thousands of micrometer-sized, individually-cladded optical fibers fused together in a single flexible-fiber format.

The present imaging fiber electrodes (IFE) combined with chemical sensors are termed herein "imaging fiber electrode chemical sensors (IFECSs)". As shown in FIG. 1a, the high resolution imaging fiber 1 at the core of the imaging fiber chemical sensors is comprised of thousands of individual ~3-micrometer diameter optical fibers 3 melted and drawn together such that an image can be carried and maintained in a coherent manner from one end to the other. Typically, the distal surface of a 350-micrometer-diameter optical fiber bundle 5, containing ~6000 optical sensors, is coated with an uniform, planar sensing layer that can measure chemical concentrations with spatial accuracy, yet is thin enough so that it does not compromise the fiber's imaging capabilities.

Figure 1B:
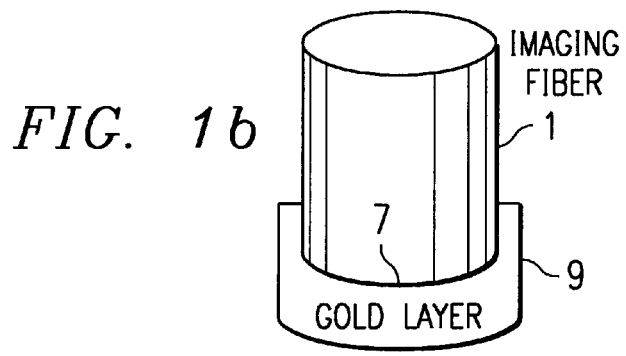
FIG. 1b: Schematic representation of an imaging fiber coated on its distal tip with a metal layer together forming an imaging fiber electrode.

As shown in FIG. 1b, an imaging fiber's distal tip 7 is metalized providing a thin metal layer 9 to serve as an electrode (i.e., an IFE) before a fluorescent redox dye is immobilized across the IFE's distal face. Although in the present examples, the imaging fibers are sputter coated with metal to serve as an electrode, alternate methods of metalization may be applicable if able to apply a metal film of the requisite translucence and homogeneity. On the right of FIG. 1a is a scanned white-light image 11 of a 270 diameter imaging fiber (~6000 optical fibers) acquired by an epi-fluorescence/CCD camera imaging system.

Figure 3:
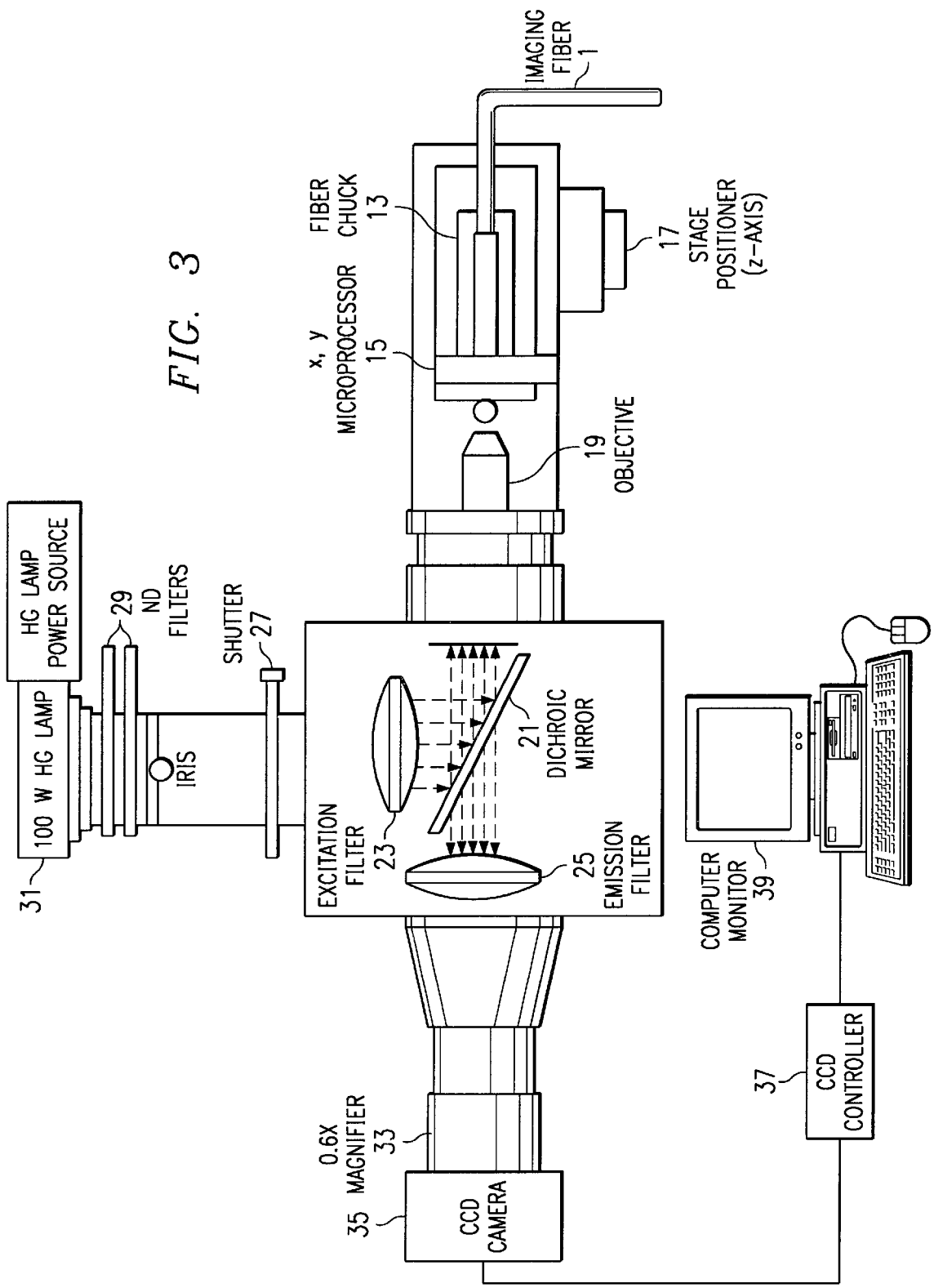
FIG. 3: Schematic diagram of an alternative embodiment of imaging fiber arrays utilized together with an epifluorescence/CCD camera imaging system according to certain aspects of the present invention.

FIG. 3 depicts an embodiment of an imaging system suitable for use with the present optical electrochemical sensors. Fluorescence and electrogenerated chemiluminescence (ECL) measurements and imaging were acquired with a modified epi-fluorescence microscope (Labophot 1A; Nikon, Irving, Tex.) which was transformed from a vertical to a horizontal position so as to accommodate both flexible and non-flexible imaging fibers (FIG. 3). In fluorescence imaging mode, the excitation from a 75-W xenon-arc lamp 31 was collimated and passed through a neutral density filter(s) 29 to control the excitation intensity. A shutter 27 could be used when desired to shut off the excitation radiation. The radiation was passed through the chosen excitation filter 23, reflected 90° by the chosen dichroic mirror 21, and focused on the imaging fiber's proximal face by a 10× or 20× E-Plan microscope objective 19. The light was transmitted through the imaging fiber 1 to the fiber's distal face where it excited the immobilized fluorescent sensing dye.

It will be recognized that the types of applicable light energy absorbing dyes, dye formulations, and dye mixtures comprising the thin film do not depend for effectiveness on a single type of light source. Light energy of determinable wavelengths may be provided by for example light emitting diodes (LED's), lasers, laser diodes and filament lamps whose light energy may be controlled by filters, including excitation and emission filters, polarizing filters, selectively reflective optical filters, diffraction gratings, optical prisms and/or cubes, beam splitters, lenses, including collimating lenses, or other optical/spectral elements. These are not exclusively the only source of useful light energy as in certain applications light energy sources such as chemiluminescence and/or bioluminescence may be employed.

Relative positioning of the objective and the imaging fiber held by fiber chuck 13 was effected by stage positioner 17 for the z axis and micropositioner 15 for the x,y axis. The returning fluorescence was transmitted through the same imaging fiber 1 and collected by the same microscope objective 19. The fluorescence light was passed through the chosen dichroic mirror 21, filtered by the chosen emission filter 25, with magnification affected if desired by a magnifier 33. The fluorescent image was captured by a charge coupled device (CCD) camera 35 under control by a CCD controller 37. The 512×768 pixel, 1-MHZ, −15° C., 12-bit CCD camera was purchased from Princeton Instruments (MicroMax; Trenton, N.J.). In ECL imaging mode, the excitation lamp was not utilized and the potentiostat was used to apply a constant potential to the imaging fiber electrode (IFE) Sensor. The IFE's sensing layer's emission was collected in the same manner as described above. All luminescence images were analyzed and CCD parameters were controlled using a Pentium-II PC 39 and WinView image-processing software (Princeton Instruments).

Figure 2:
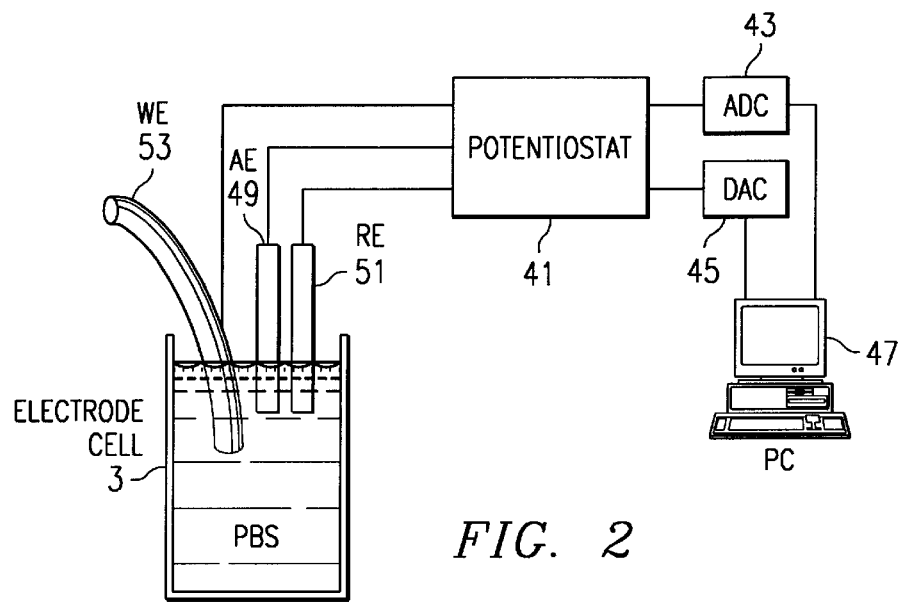
FIG. 2: Schematic diagram of the one embodiment of electrochemical instrumentation comprising a potentiostat, an analog-to-digital converter (ADC), a digital-to-analog converter (DAC), a PC, and a three electrode cell (comprising a working electrode (WE), an auxiliary electrode (AE), and a reference electrode (RE)).

As shown in FIG. 2, staircase cyclic voltammetry (typically 0.5 V/s) was performed with an EI-400 bipotentiostat 41 (Ensman Instrumentation, Bloomington, Ind.). All waveforms were generated and currents acquired via an A/D 43–D/A 45 interface (Labmaster DMA; Scientific Solutions, Solon, Ohio) that was interfaced to a Pentium-II PC 47. BEWK electrochemistry software (Cypress System Inc., Lawrence, Kans.) was used to control electrochemical parameters and to collect and process data. For cyclic voltammetric studies, 250-micrometer diameter gold disk electrodes, 1-mm diameter platinum disk electrodes (Cypress System, Inc.), IFEs, and IFECSs were employed as the working electrode (WE) 53. All working electrodes (except IFEs and IFECSs) were polished on fresh lapping films followed by sonication in deionized water for 30 s. An Ag/AgCl reference electrode (RE) 51 and a platinum wire auxiliary electrode (AE) 49 were employed.

In the following examples the electrochemically-modulated, imaging fiber chemical sensors of the present invention are designed for the detection of specific analytes.

EXAMPLE 1

Figure 5:
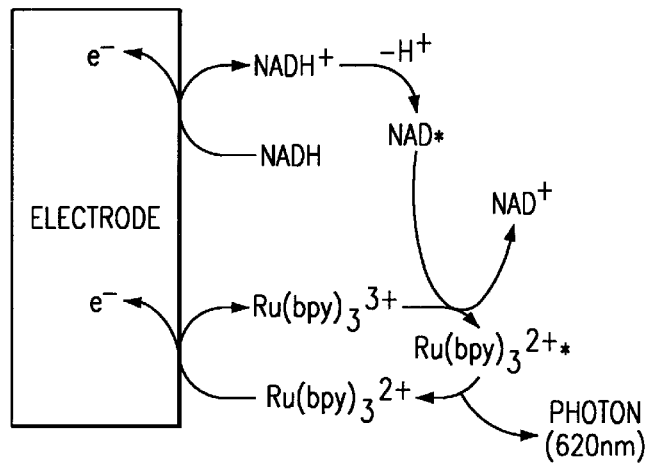
FIG. 5: Schematic diagram of a possible ECL reaction mechanism involving NADH and $Ru(bpy)_3^{2+}$.

Electrochemically-Modulated, Chemiluminescence-Based Imaging Fiber Chemical Sensors for TEA and NADH The term chemiluminescence covers those light-emission processes which accompany certain chemical reactions. One unfortunate aspect of many luminophores (e.g., luminol) is that they are irreversibly consumed during the chemiluminescence reaction, and thus, they are limited to single-use fiber-optic probes or to applications employing flowing streams [Robards, K. & Worsfold, P. J. (1992) *Anal. Chim. Acta* 266:147]. One luminophore that can be (electro) chemically regenerated is tris(2,2'-bipyridine)ruthenium(II), $Ru(bpy)_3^{2+}$ [Xu, X.-H.& Bard, A. J. (1994) *Langmuir* 10:2409]. Recently, Neiman and co-workers have shown that the electrogenerated chemiluminescence (ECL) of $Ru(bpy)_3^{2+}$ contained in a NAFION film on a solid working electrode can be used to detect NADH [Downey, T. M. & Nieman, T. A. (1992) *Anal Chem* 64:261]. In brief, after $Ru(bpy)_3^{2+}$ is oxidized to $Ru(bpy)_3^{3+}$ at a properly poised electrode surface, the reaction of NADH with $Ru(bpy)_3^{3+}$ produces the excited Ru(II) complex, $\{Ru(bpy)_3^{2+}\}^*$. The return of the excited ruthenium(II) complex to the ground state is accompanied by a concurrent chemiluminescence emission (FIG. 5). FIG. 5 further shows that NADH and $Ru(bpy)_3^{2+}$ are both oxidized at an electrode surface. The one-electron-oxidized cation radical $NAD^{•+}$ loses a proton to become a strongly reducing radical, $NAD^{•}$. $NAD^{•}$ transfers an electron to $Ru(bpy)_3^{3+}$ to form $NAD^+$ and the excited-state species, $Ru(bpy)_3^{2+*}$. $Ru(bpy)_3^{2+*}$ emits a photon when it decays to the ground state; therefore, the ECL reactions result in $Ru(bpy)_3^{2+}$ reformation. The process can be repeated when $Ru(bpy)_3^{2+}$ is electrochemically recycled to $Ru(bpy)_3^{3+}$ at the electrode surface. While optical images of the ECL emanating from these electrode surfaces have been acquired, [Shultz, L. L. et al.(1996) *Anal. Chem.* 68:349] to date no ECL imaging sensors have been fabricated using this approach.

Figure 6:
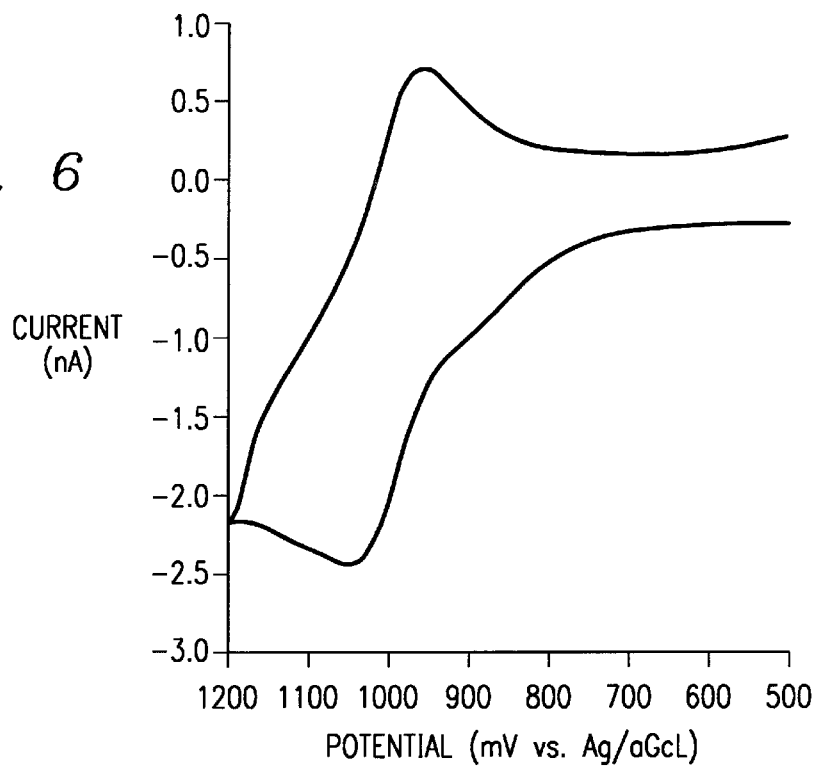
FIG. 6. Representative single scan $Ru(bpy)_3^{2+}$ CV (0.5 V/s; 12-Hz filter) acquired from a gold electrode immersed in 2 mM $Ru(bpy)_3^{2+}$/KCl-PBS (n>20 electrodes tested).

$Ru(bpy)_3^{2+}$ cyclic voltammetry was performed at gold, platinum, and carbon electrodes in order to evaluate the best metal for sputter coating imaging fiber distal faces. In all three cases, quasi-reversible voltammetry was observed with the fastest electron transfer kinetics being observed at gold and carbon surfaces. For example, the $Ru(bpy)_3^{2+}$ oxidation peak potential and $\Delta E_p$ at the gold electrode were typically ~1056 mV and ~104 mV, respectively (FIG. 6).

Figure 7:
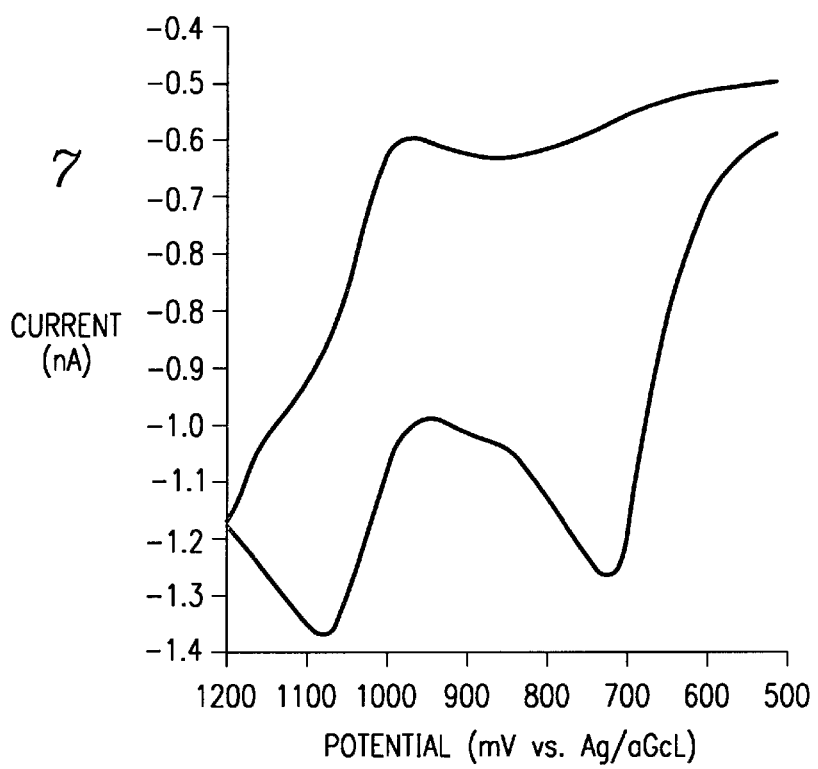
FIG. 7. Representative single scan NADH+$Ru(bpy)_3^{2+}$ CV (1.0 V/s; 24-Hz filter) acquired from a gold electrode immersed in (10 mM $Ru(bpy)_3^{2+}$+20 mM NADH)/KCl-PBS (n>5 electrodes tested).

Cyclic voltammetry was performed in solutions containing $Ru(bpy)_3^{2+}$ and NADH (FIG. 7). The oxidation of NADH is chemically irreversible due to rapid protonation kinetics occurring in the $NAD^+/NAD^{•}$ redox couple; in addition, the electrochemical oxidation of NADH shows a large overpotential at most electrode surfaces as its formal potential ($E^{o\prime}$) is −0.56 V vs. SCE (as shown by work including that of one of the present inventors: Kuhr, W. G., Barrett, V. L., Gagnon, M. R., Hopper, P., Pantano, P. (1993) *Anal Chem* 65:617). At each surface, the major NADH oxidation peak was distinct from the $Ru(bpy)_3^{2+}$ redox couple. For example, the oxidation peak potentials for $Ru(bpy)_3^{2+}$ and NADH at the gold electrode were typically ~1087 mV and ~700 mV respectively (FIG. 7).

While quasi-reversible $Ru(bpy)_3^{2+}$ CVs (±NADH) were observed at carbon, platinum and gold electrodes, quasi-reversible $Ru(bpy)_3^{2+}$ voltammograms (FIG. 8) were obtained only at gold sputter-coated imaging fibers (IFEs) using the reagents and method of the present example. Using MPS-silization, voltammetry experiments with gold IFEs, the $\Delta E_p$ for $Ru(bpy)_3^{2+}$ at a properly prepared gold IFE (FIG. 8) was nearly identical to that observed at a gold electrode as shown in FIG. 6.

Figure 9:
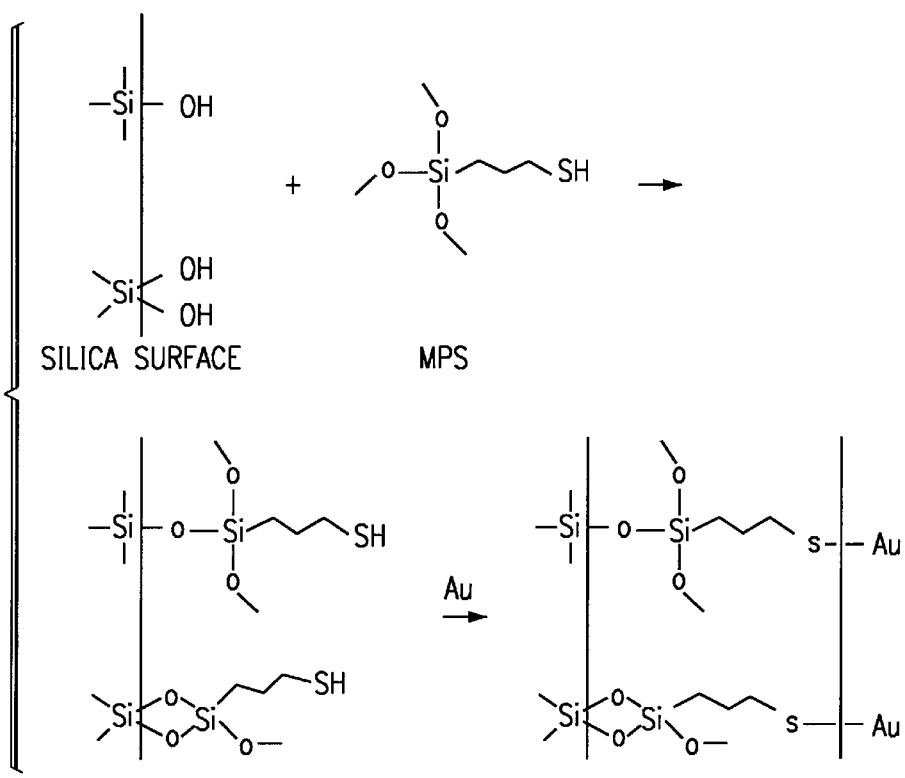
FIG. 9. Schematic diagram of the MPS/silica silanization and gold coating reactions. The silica surface was MPS-treated and the thiol-derivatized surface was gold coated.

Using MPS-silanization presumably occurring as shown in FIG. 9, acceptable gold adhesion was obtained. In comparing MPS-treated and untreated glass slides, gold was removed from the untreated glass by a 3-minute water spray, gold was not removed from the MPS-treated glass after a 5-minute water spray. Although MPS silization was found to be efficacious, it is anticipated and within the scope of the present invention to apply various conductive layers according to various techniques or adhesive processes wherein the conductive layer has characteristics of sufficient adhesion, quasi-reversible electroconductivity and optical transmissibility.

Figure 10:
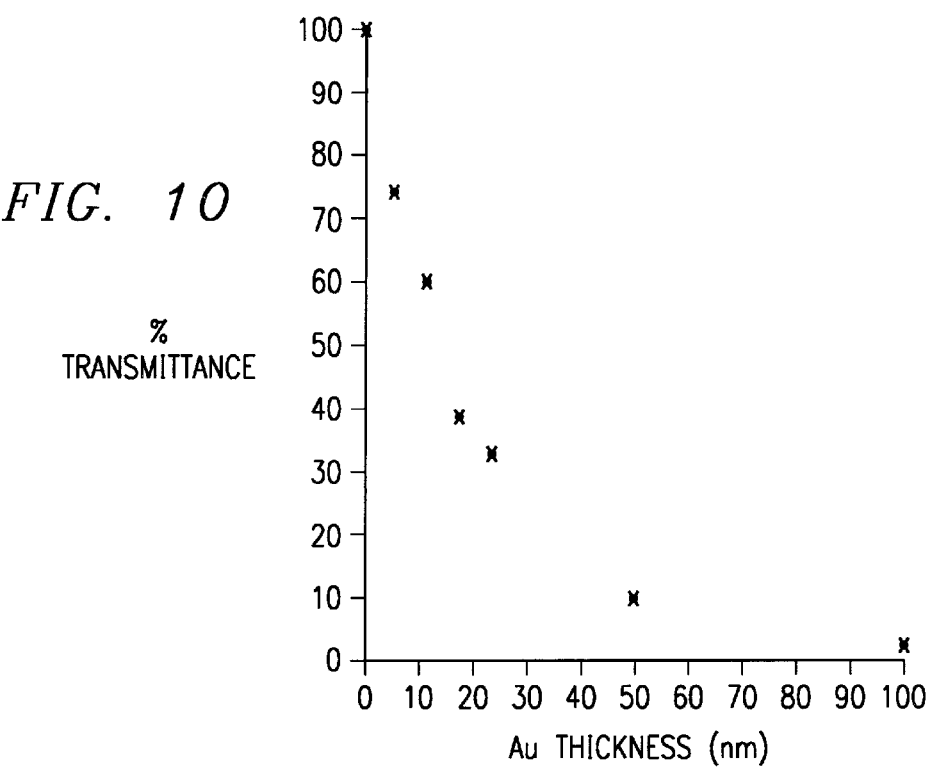
FIG. 10. Plot of gold thickness vs. percent transmittance where an optical power meter was used to measure light transmittance through bare and gold-coated imaging fibers.

While an adhesive gold layer was important for electrochemistry, a thin transparent layer was important for ECL imaging. The light transmittance through bare and gold-coated imaging fibers was characterized using an optical power meter. The percent transmittance of light that was decreased by increasing the gold film thickness is shown in FIG. 10. The percent transmittance of light through a 100-nm thick gold film was ~3% and that for a ~23-nm thick gold film was ~32%. While higher transmittance was observed through thinner films, there were electrical contact problems when the film thickness was less than 20 nm. Since quasi-reversible $Ru(bpy)_3^{2+}$ cyclic voltammetry was observed at thick ($\geq$70 nm) gold IFEs (FIG. 8), and since the $Ru(bpy)_3^{2+}$ cyclic voltammetry observed at ~23-nm thick gold IFEs was similar (data not shown), gold IFEs of the present example (i.e., MPS-silanized gold IFEs) were sputter-coated with ~23-nm thick gold layers.

In the present example, NAFION was again chosen as the immobilization polymer. In addition to other desirable characteristics, NAFION also provides selectivity against anions in that it can exclude them from reaching an electrode surface and being detected [Kristensen, E. W. et al.(1987) *Anal. Chem.* 59:1752].

Figure 11:
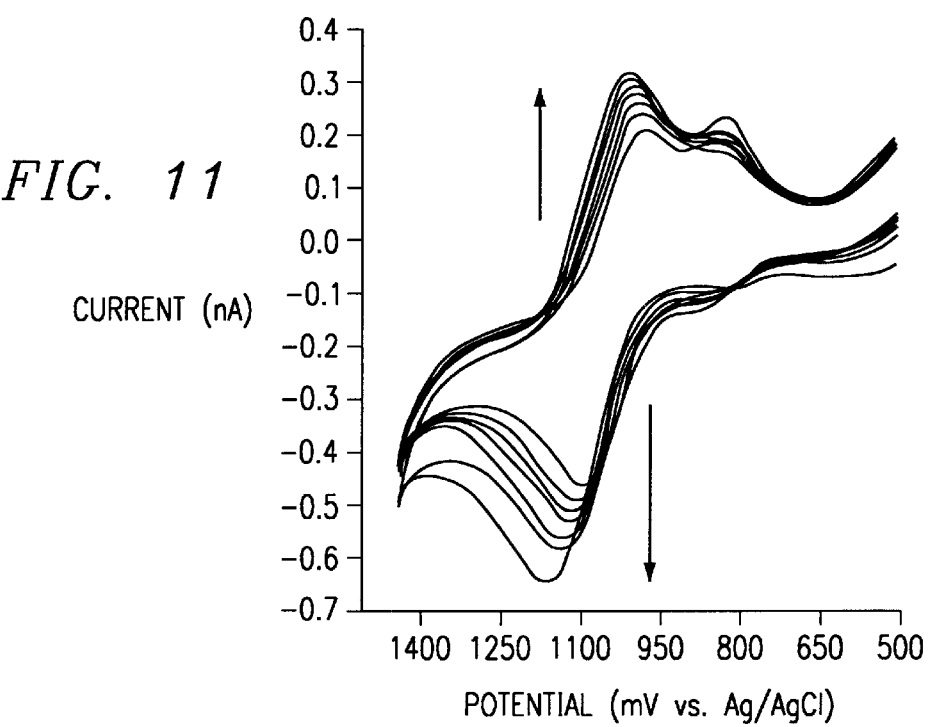
FIG. 11: Representative single scan $Ru(bpy)_3^{2+}$ CVS (0.1 V/s; 2.4-Hz filter) acquired from a NAFION dip-coated gold electrode immersed in 1 mM $Ru(bpy)_3^{2+}$/0.1 M $H_2SO_4$ solution.

Using gold electrodes, $Ru(bpy)_3^{2+}$ incorporation into NAFION was monitored via repetitive cyclic voltammetry. In general, for ion-containing polymers such as NAFION, "effective" diffusion coefficients are utilized since electron hopping, counter ion movement, and actual diffusion contribute to the observed rate of charge transfer through the film; the effective diffusion coefficient for $Ru(bpy)_3^{2+}$ in NAFION is ~$10^{-10}$ cm$^2$/s (see Henning, T. P. et al.(1981) *J. Am. Chem. Soc.* 103:3937 and citations within). A NAFION-modified gold electrode was soaked in a 1 mM $Ru(bpy)_3^{2+}$/ 0.1 M $H_2SO_4$ solution and 46 CV scans were obtained (FIG. 11). In FIG. 11, the seven (10th, 16th, 21st, 25th, 26th, 31st, and 46th) single-scan CVs demonstrate $Ru(bpy)_3^{2+}$ incorporation into the NAFION film; the arrows denote increasing scan numbers. As the scan number increased (i.e., as the soaking time increased), the magnitude of the $Ru(bpy)_3^{2+}$ oxidation and reduction peak currents increased. Since the magnitude of the oxidation and reduction peak currents was directly proportional to the Ru(bpy)$_3^{2+}$ concentration in NAFION film, the voltammetric data indicated that the NAFION layer was saturated with Ru(bpy)$_3^{2+}$ after ~50 scans. Therefore, the IFE-Sensors were fabricated with a 60-min Ru(bpy)$_3^{2+}$ soaking time.

Figure 8:
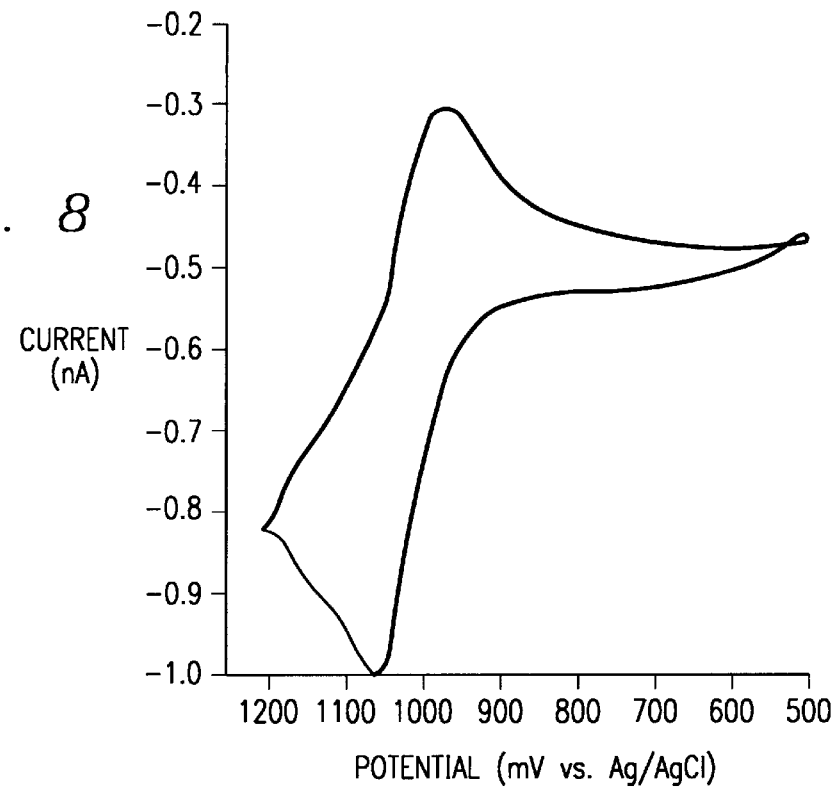
FIG. 8. Representative single scan $Ru(bpy)_3^{2+}$ CV (0.5 V/s; 12-Hz filter) acquired from an IFE (70-nm thick gold coating) immersed in 5 mM $Ru(bpy)_3^{2+}$/KCl-PBS (n>5 IFEs tested).
Figure 12:
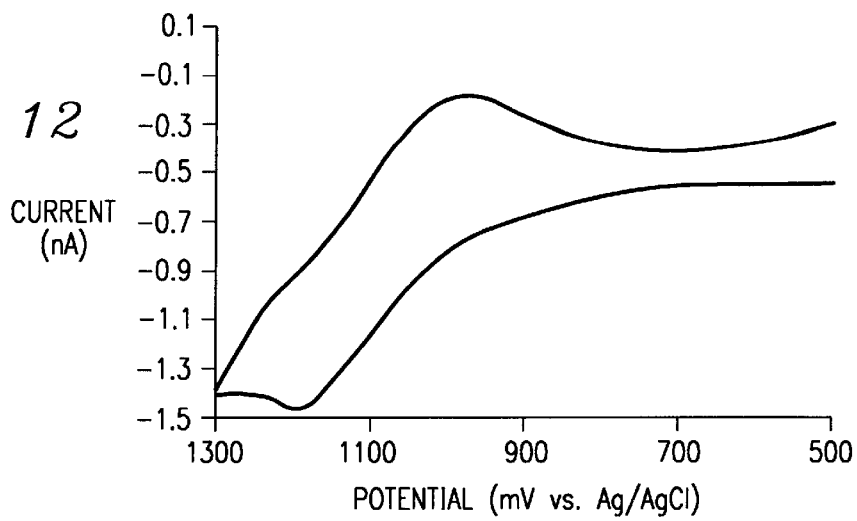
FIG. 12: Representative single scan $Ru(bpy)_3^{2+}$ CV (0.5 V/s; 12-Hz filter) acquired from an IFE-Sensor immersed in KCl-PBS (n>7 IFE-Sensors tested).

FIG. 12-top shows the CV acquired from an IFE-Sensor (i.e., a Ru(bpy)$_3^{2+}$/NAFION-modified, gold-coated, MPS-silanized imaging fiber) immersed in KCl-PBS. While the Ru(bpy)$_3^{2+}$ reduction peak potential (~965 mV) was similar to that observed at bare gold electrodes (FIG. 6) and gold IFEs (FIG. 8) immersed in Ru(bpy)$_3^{2+}$/KCl-PBS, the oxidation peak potential was shifted ~120–140 mV positive relative to that observed at gold electrodes (FIG. 6) and gold IFEs (FIG. 8). In other words, Ru(bpy)$_3^{2+}$ heterogeneous electron transfer kinetics were slower at the IFE-Sensor (FIG. 12, top). Interpretation of cyclic voltammetric peak shapes and positions for ion-containing polymers is difficult because these CVs reflect the kinetics and thermodynamics of various processes and properties such as charge-transfer mechanisms, film reorganization kinetics, formal potentials, and heterogeneous electron transfer kinetics (see Martin, C. R. et al.(1982) *J. Am. Chem. Soc.* 104:4817 and citations within). Furthermore, in this work, the voltammetric observations can be attributed additionally to sputter-coated gold surface variations, and the differences between gold electrode surfaces (i.e., solid gold wires) and <100-nm thick sputter-coated gold imaging fiber surfaces. Nonetheless, this example provides a demonstration of Ru(bpy)$_3^{2+}$ incorporation into gold-coated imaging fiber NAFION layers.

Figure 13:
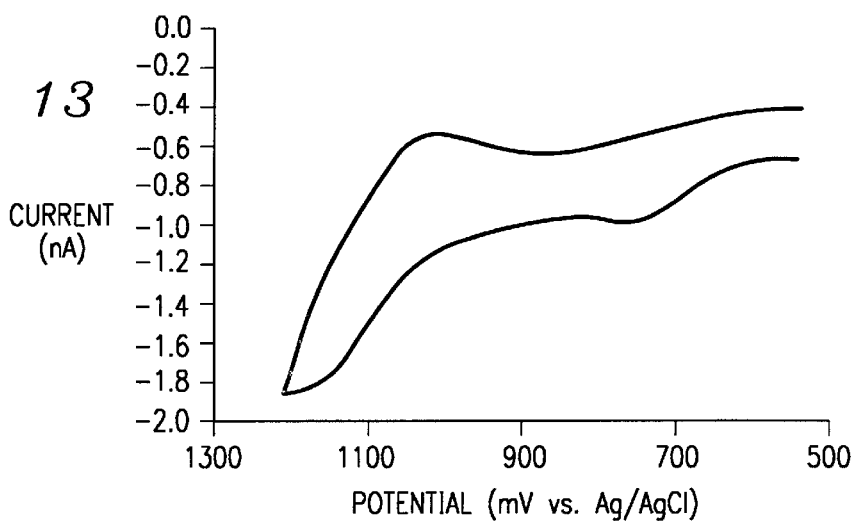
FIG. 13: Representative single scan NADH+$Ru(bpy)_3^{2+}$ CV (0.5 V/s; 12-Hz filter) acquired from a different IFE-Sensor immersed in 20 mM NADH/KCl-PBS (n>4 IFE-Sensors tested).

FIG. 13 shows a CV acquired from an IFE-Sensor immersed in 20 mM NADH/KCl-PBS. While the NADH oxidation peak was distinct from the Ru(bpy)$_3^{2+}$ oxidation peak (as observed previously; see FIG. 7, the NADH oxidation peak at ~700 mV was typically very minute at IFE-Sensors. Nonetheless, these data demonstrate NADH diffusion through the NAFION layer.

In another example, TEA was used as a standard for ECL imaging because a similar molecule, tripropylamine, was reported to generate intense ECL emission [Shultz, L. L. et al. (1996) *Anal. Chem.* 68:349]. A bright and uniform ECL image obtained by applying +1.3 V to an IFE-Sensor immersed in TEA demonstrated the success of the IFE-Sensor fabrication steps.

A weaker but clearly identifiable ECL image was similarly obtained by applying +1.3 V to an IFE-Sensor immersed in NADH/pH 5.5 NaNO$_3$-PBS. When the constant +1.3 V potential was applied to the IFE-Sensor, the orange ECL emission was visible to a dark-room adapted eye. It is anticipated and within the scope of the present invention to coat the imaging fiber with other optically-transparent conductive material such as, for one example, Indium Tin Oxide (ITO). ITO is an attractive surface since it can be readily silanized with a variety of organosilanes according to methods known in the art. [Such as for example, Murray, R. W.; Bard, A. J., Ed.; Marcel Dekker: New York, 1984; Vol. 13, pp 191–368]. Thus, covalent attachment schemes could be employed to immobilize suitable dye molecules to the modified-ITO surface. Recently, derivatized-Ru(bpy)$_3^{2+}$ complexes of the type described in Richter, M. M. et al. (1998) *Anal. Chem.* 70, 310–318 and Zhang, X. & Bard, A. J. (1992) *J. Phys. Chem.* 5566–5569 have been attached covalently to electrode surfaces by methods such as those described in Abruna, H. D. et al. (1979) *Inorg. Chem.* 11, 3233–3240; Abruna, H. D. et al. (1981) *Inorg. Chem.* 20, 1481–1486; Friesen, D. A. et al. (1998) *Inorg. Chem.* 37, 2756–2762; Dupray, L. M.& Meyer, T. J. (1996) *Inorg. Chem.* 35, 6299–6307. It is anticipated that such an approach could eliminate the need for the adhesive polymer NAFION layer. This might be advantageous since it can be rationalized that NAD$^+$, a NADH oxidation product, accumulates in the NAFION layer and that such NAD$^+$ accumulation could hinder NADH diffusion into the NAFION layer. It is further anticipated that such improvements should permit IFE-Sensor analytical performance features such as sensitivity, selectivity, and temporal responses to be evaluated and exploited for the quantitation of NADH from biological cells and tissue Reagents and Materials Tris(2,2'-bipyridyl)ruthenium(II) chloride hexahydrate (Ru(bpy)$_3^{2+}$), (3-mercaptopropyl)trimethoxysilane (MPS), triethylamine (TEA), sodium nitrate (NaNO$_3$), and NAFION were purchased from Aldrich Chemical Co. (Milwaukee, Wis.). Acetone (optima grade), sodium phosphate (dibasic heptahydrate and monobasic dihydrate), and potassium chloride (KCl) were obtained from Fisher Chemical (Houston, Tex.). Isopropyl alcohol, and concentrated sulfuric acid were obtained from EM Science (Gibbstown, N.J.). b-nicotinamide adenine dinucleotide, reduced form (NADH) was purchased from Sigma Chemical Co. (St. Louis, Mo.). Hydrogen peroxide (30%) was obtained from Advanced Chemical Systems International Inc. (Milpitas, Calif.). Argon gas (99.99+%) was purchased from Air Liquide (Grand Prairie, Tex.). All chemicals were used as received without further purification. Deionized water (18 Megaohm-cm) was obtained using a Nanopure Infinity water purification system (Barnstead; dubuque, Iowa). Piranha solution was prepared by mixing 30% hydrogen peroxide and concentrated sulfuric acid in 1:4 ratio. The MPS silanization solution was prepared by adding 1 g MPS to a mixture of 1 g deionized water and 40 g isopropyl alcohol. A pH 7.0, 200 mM KCl/10 mM PBS (KCl-PBS) was prepared by mixing ~350 mL of a 10 mM dibasic phosphate/200 mM KCl solution and ~200 mL of a 10 mM monobasic phosphate/200 mM KCl solution. A pH 7.0, 200 mM NaNO$_3$/10 mM PBS (NaNO$_3$-PBS) was prepared by mixing ~350 mL of a 10 mM dibasic phosphate/200 mM NaNO$_3$ solution and ~200 mL of a 10 mM monobasic phosphate/200 mM NaNO$_3$ solution. NADH solutions (1–60 mM) were prepared with KCl-PBS or NaNO$_3$-PBS. 5 mM TEA solution was prepared by diluting 3.5-mL of 7.1 M TEA with 5 mL KCl-PBS.

Silica imaging fibers with a ~350-micrometer total diameter comprising ~6000 individually cladded ~3-micrometer diameter optical fibers were purchased from Sumitomo Electric Industries (Part No. IGN-035/06; Torrance, Calif.). The coherent fiber-optic bundle's active imaging diameter was ~270 micrometer (i.e., the individual optical fibers were fused within a ~15-micrometer thick silica tube and this tube was coated with a ~25-micrometer thick silicone jacket). Lapping films with abrasive sizes of 12-, 3-, 1-, and 0.3-micrometer were obtained from Mark V Laboratory (East Grandy, Conn.). The fiber polishing chuck was purchased from General Fiber Optics (Model No. 30-21; Fairfield, N.J.). Glass microscope slides (7.54 cm×2.54 cm) were obtained from Corning Glass Works (Corning, N.Y.).

Imaging Fiber Electrode (IFE) Sensor Fabrication

IFE Sensor preparation began by cleaving both imaging fiber ends with a sapphire scribe and removing the ~1-inch long fiber jacket from the imaging fiber's distal end with acetone.

The imaging fiber was secured in an appropriate fiber chuck and both fiber faces were polished successively on 12-, 3-, 1-, and 0.3-micrometer lapping films. Polishing was accomplished by maneuvering a secured fiber's face in a figure eight-like fashion over each abrasive surface. The fiber's face was sonicated in deionized water between each successive film to remove fiber and abrasive particles. All polished fiber faces were inspected under a Bausch and Lomb stereo-zoom microscope (30×magnification) for macroscopic scratches. The ~1-inch long imaging fiber's distal tip was cleaned chemically by soaking in Piranha solution at 70° C. for 20 min. The distal end was rinsed with deionized water, dried in air for 30 min, and dried in an oven at 105° C. for 10 min.

To enhance gold film adhesion to the imaging fiber's silica surface, the fiber's polished distal face was silanized with MPS. The fiber's distal tip was immersed in refluxing MPS solution for 10 min, rinsed with isopropyl alcohol, dried in air for 20 min, and dried in an oven at ~100° C. for 8 min. The process of MPS immersion, rinsing, and drying was performed three times.

Hummer model VII sputtering coater (Anatech Ltd., Springfield, Va.) was used for gold film deposition on fiber distal faces. The imaging fiber's MPS-silanized distal tip was mounted vertically on the platform inside the sputter coater's chamber such that the fiber distal face was normal to the 100% gold target. The sample chamber was evacuated to ~40 mtorr, argon gas (~80 mtorr) was introduced into the chamber, and the fiber's distal tip was gold coated at a 3-nm/min rate until a ~23-nm thick gold coating was obtained. Unless noted otherwise, all IFEs and IFE-Sensors had a ~23-nm thick gold coating.

NAFION spin-coating was performed with a Servodyne mixer/spinner having an inverted mixer-head with a digital RPM controller (Cole-Parmer Instrument Co., Veron Hills, Ill.). The imaging fiber's gold-coated distal tip was mounted vertically into the spinner's mixer-head. A 25-microliter NAFION aliquot was dispensed onto the fiber's gold coated surface, the fiber was spun at 2000 RPM for 1 min, and dried in air for 15 min. The process was repeated and the NAFION coated fiber was dried in air for at least 30 min before further processing. The NAFION-modified imaging fiber was soaked in 0.1 M $H_2SO_4$ for 1 h according to the procedure of Nieman and co-workers to permit NAFION swelling.

Figure 4:
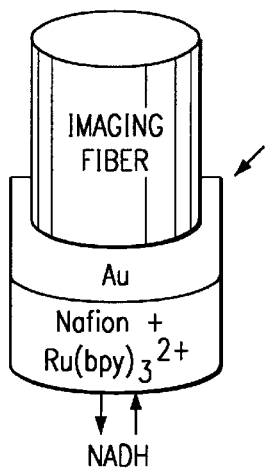
FIG. 4: Schematic diagram of a $Ru(bpy)_3^{2+}$-IFE-Sensor. The arrow indicates the electrical contact region.

The gold-coated, sulfuric acid-treated, NAFION-modified imaging fiber was soaked in 5 mM $Ru(bpy)_3^{2+}$/0.1 M sulfuric acid for 1 h according to the procedure of Nieman and co-workers. The conformation of the resulting sensor is depicted in FIG. 4. All IFE Sensors were stored in deionized water.

Cyclic Voltammetric Studies

For cyclic voltammetric studies, 3-mm diameter carbon, 250-micrometer diameter platinum, 250-micrometer diameter gold electrodes (Cypress System Inc.) and IFEs were used. All electrodes (except IFEs) were polished on 12-, 3-, 1-, and 0.3-micrometer lapping films followed by sonication in deionized water for ~10 s after each step to remove particulate material. In all cases, a three electrode cell was used: a carbon, platinum, or gold electrode or IFE served as the working electrode (WE), a platinum wire was used as the auxiliary electrode (AE), and a Ag/AgCl wire was used as the reference electrode (RE). All cyclic voltammetry was performed in PBS.

$Ru(bpy)_3^{2+}$ Fluorescence Imaging $Ru(bpy)_3^{2+}$ fluorescence images were obtained using the epi-fluorescence microscope/CCD imaging system. The IFE sensor's distal end was placed in air-saturated PBS and the fiber's proximal end was mounted onto the epi-fluorescence microscope stage. A custom filter cube (Omega Optical, Brattleboro, Vt.) comprising a 485±11-nm excitation filter, a 605±25-nm emission filter, and a 540-nm dichroic mirror was used. Two neutral density filters (ND 2.0+ND 4.0) were used to reduce the excitation light intensity in order to minimize photobleaching during the imaging process. The CCD exposure time was typically 1.5 s.

$Ru(bpy)_3^{2+}$ ECL Imaging $Ru(bpy)_3^{2+}$ ECL images were obtained using the epi-fluorescence microscope/CCD imaging system. The IFE sensor's distal end was placed in a NADH (or TEA) solution and the fiber's proximal end was mounted onto the epi-fluorescence microscope stage. In general, only a 605±25-nm emission filter was used. The CCD exposure time was typically 20 s, and the applied potential was +1.3 V vs. Ag/AgCl.

EXAMPLE 2

Figure 14:
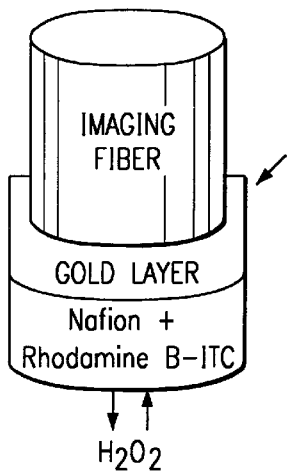
FIG. 14: Schematic diagram of the distal tip of a RBITC-imaging fiber electrode chemical sensor (i.e., a RBITC-IFECS).
Figure 15:
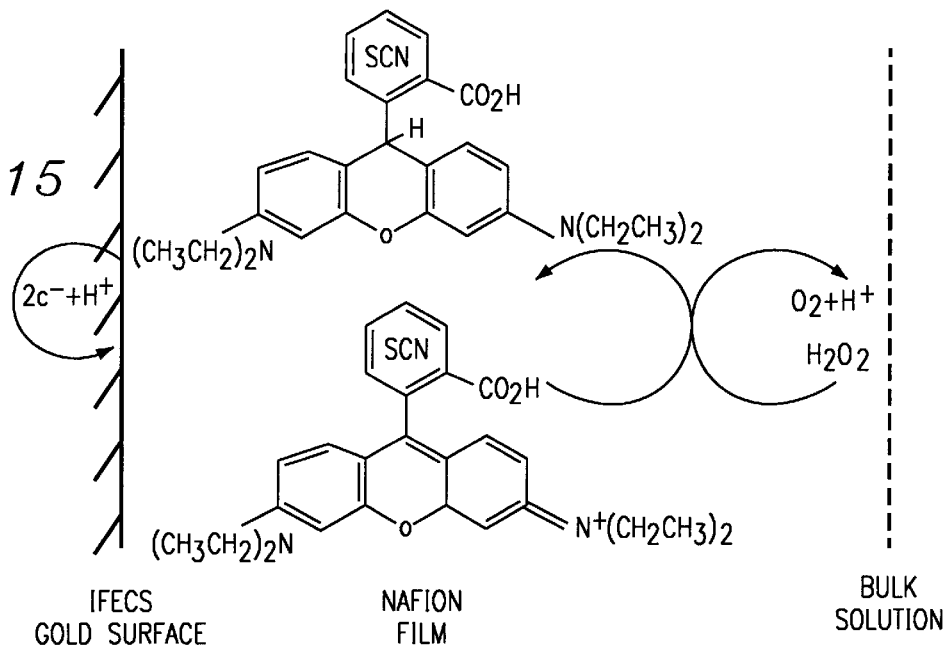
FIG. 15: Schematic diagram of a RBITC-IFECS sensing layer and possible homogeneous and heterogeneous electron transfer reactions after hydrogen peroxide diffuses into the NAFION layer.

Electrochemically-Modulated, Fluorescence-Based Imaging Fiber Chemical Sensors for Hydrogen Peroxide As one example of an embodiment of an electrochemically-modulated, fluorescence-based, imaging fiber electrode chemical sensor (IFECS), the design involved immobilizing a fluorescent redox dye across an IFE's distal face such that hydrogen peroxide could be imaged through the IFECS itself (FIG. 14). This was accomplished by monitoring the change in fluorescence of the immobilized fluorescent redox dye following its homogeneous electron transfer reaction with hydrogen peroxide (FIG. 15). IFECS reversibility was demonstrated by applying a suitable potential across the IFECS to regenerate the immobilized fluorescent redox dye.

Over a dozen fluorescent redox dye candidates (e.g., nile blue A, rhodamine 123, rubrene, rhodanile blue) were evaluated with respect to their electrochemical properties, their hydrogen peroxide reactivity, their polymer leaching properties, their pH sensitivities, etc. Although certain of these dyes may be desirable in certain alternate applications, rhodamine B isothiocyanate (RBITC) was found to be applicable in the present example due to its relatively high fluorescence quantum yield and dioxygen insensitivity.

Figure 16:
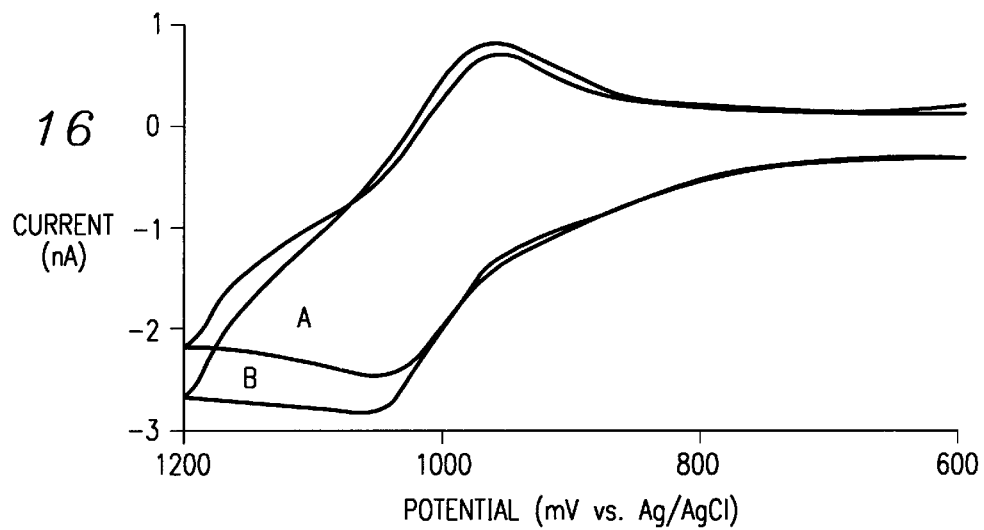
FIG. 16: Representative single-scan $Ru(bpy)_3^{2+}$ cyclic voltammograms (1 V/s; 24-Hz filter) acquired from a solid gold disk electrode (A) and an imaging fiber electrode (B) immersed in 5 mM $Ru(bpy)_3^{2+}$/PBS.

$Ru(bpy)_3^{2+}$ cyclic voltammetry was performed using solid disk electrodes as a performance standard for development of optical fiber electrodes. Although alterative procedures may be employed to generate the instant IFECSs, in the present example fabrication was conducted in a stepwise fashion with concomitant stepwise characterization via fluorescence imaging and cyclic voltammetry. In the present example, $Ru(bpy)_3^{2+}$ was chosen as an exemplary redox species to evaluate various metalized imaging fiber surfaces. Specifically, $Ru(bpy)_3^{2+}$ cyclic voltammetry was performed at solid gold and platinum disk electrodes in order to evaluate the applicability of various metals for sputter coating imaging fiber distal faces (n>100 electrodes tested). The $Ru(bpy)_3^{2+}$ redox couple is believed to undergo a fast, outer-sphere, one-electron transfer reaction at solid electrodes; the $Ru(bpy)_3^{2+}$ formal potential ($E°$) is +1.03 V vs. SCE [R. L. McCreery, in A. J. Bard (Ed.), Electroanalytical Chemistry (Vol. 17), Marcel Decker, New York, 1991, p. 221]. Quasi-reversible voltammetry was observed for the $Ru(bpy)_3^{2+}$ redox couple at solid gold and platinum electrode surfaces. For example, the $Ru(bpy)_3^{2+}$ oxidation peak potential and $\Delta E_p$ at gold electrodes were typically ~1060 mV and ~100 mV, respectively (FIG. 16,A).

Quasi-reversible $Ru(bpy)_3^{2+}$ voltammetry (FIG. 16,B) was also observed for gold sputter-coated imaging fibers (IFEs). The initial voltammetry experiments with gold IFEs demonstrated the need for strong gold-silica adhesion in order to obtain reproducible voltammetry. As such, a method for obtaining strong gold-silica adhesion on optical fibers was developed by modification of methods of MPS-silanization known in the art [Goss, C. A., Charych, D. H. & Majda, M.(1991) Anal. Chem.63:85]. In conjunction with Piranha solution cleaning, MPS-silanization improved sputter-coated gold adhesion to imaging fiber surfaces. The $\Delta E_p$ for $Ru(bpy)_3^{2+}$ at properly-prepared gold IFEs (FIG. 16,B) was nearly identical to that observed at solid gold disk electrodes (FIG. 16,A).

While a robust gold layer was important for electrochemistry, a semi-transparent layer was important for fluorescence imaging. The light transmittance through bare and gold-coated imaging fibers was characterized using an optical power meter. As expected, the percent transmittance of light decreased as the gold film thickness was increased. Specifically, the percent transmittance of light through a ~100-nm thick gold film was ~3% and that for a ~20-nm thick gold film was ~32%. While higher light transmittance was observed through imaging fibers coated with thinner films, there were electrical contact problems when the film thickness was <20 nm. Since quasi-reversible $Ru(bpy)_3^{2+}$ cyclic voltammetry was observed at ~20-nm thick gold IFEs (FIG. 16,B), IFEs of the present embodiment (i.e., MPS-silanized, gold IFEs) were sputter-coated with ~20-nm thick gold layers.

Figure 17:
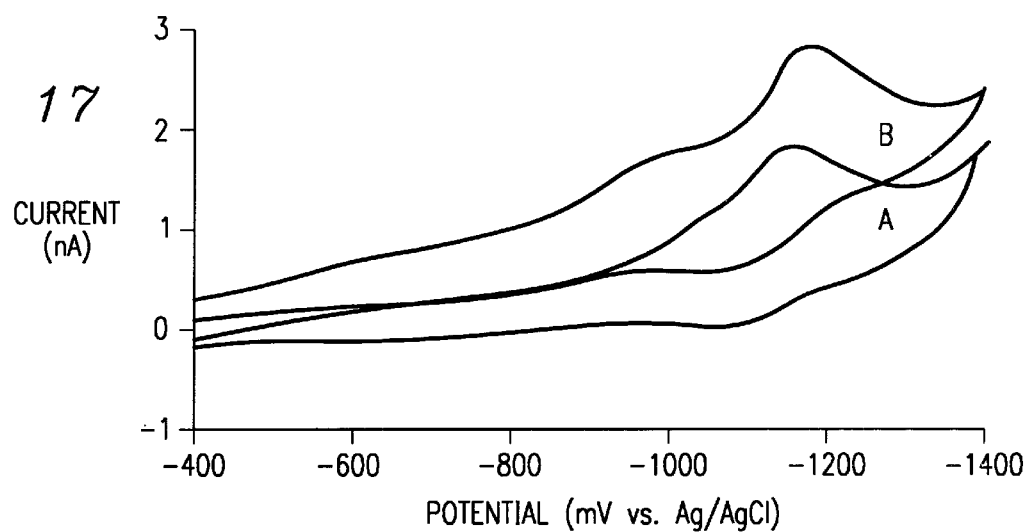
FIG. 17: Representative single-scan RBITC cyclic voltammograms (1 V/s; 24-Hz filter) acquired from a solid gold disk electrode (A) and an imaging fiber electrode (B) immersed in 5 mM RBITC/PBS.

RBITC cyclic voltammetry at solid gold disk electrodes and IFEs was compared. The electrochemical properties of RBITC at gold surfaces were evaluated by performing cyclic voltammetry with solid gold disk electrodes and IFEs immersed in RBITC solutions. Reversible voltammetry was observed for the RBITC redox couple at gold disk electrodes during reductive scans from 0 to −1400 mV (n>40 electrodes tested). For example, the RBITC reduction peak potential and $\Delta E_p$ at gold disk electrodes were ~−1160 mV and ~60 mV, respectively (FIG. 17,A). Similarly, reversible voltammetry was observed for the RBITC redox couple at IFEs during reductive scans from 0 to −1400 mV (n>10 electrodes tested). For example, the RBITC reduction peak potential and $\Delta E_p$ at IFEs were ~−1160 mV and ~60 mV, respectively (FIG. 17,B).

Imaging fiber chemical probe (IFCP) and imaging fiber electrode chemical sensor (IFECS) fabrication required the dye to be immobilized to the imaging fiber's (or the imaging fiber electrode's) distal face. Although it is anticipated that immobilization reagents could be substituted, including other polymers or polymer films, NAFION, a cation-exchange polymer, was chosen as the immobilization polymer for cationic RBITC. NAFION is chemically and thermally stable, is able to extract high concentrations of cations from dilute solutions, and can selectively decrease anionic species accumulation at NAFION-modified electrode surfaces. The chemical structure of a NAFION polymer subunit is shown below:

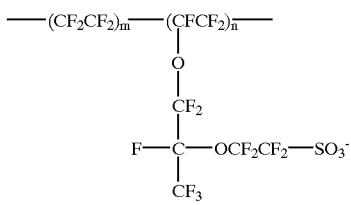

For imaging purposes, a thin, planar NAFION film was found to provide desired results. Since non-uniform, hemispherical NAFION films were observed on imaging fiber distal faces that were dip-coated in NAFION (data not shown), spin-coating techniques were employed. It is anticipated and within the scope of the present invention to employ other methods of forming a uniform layer immobilization layer. A 2000-RPM/60-s technique was found to be effective in producing a planar NAFION layers(n>30 IFCPs and IFECSs tested) and employed in the present embodiment.

Figure 19:
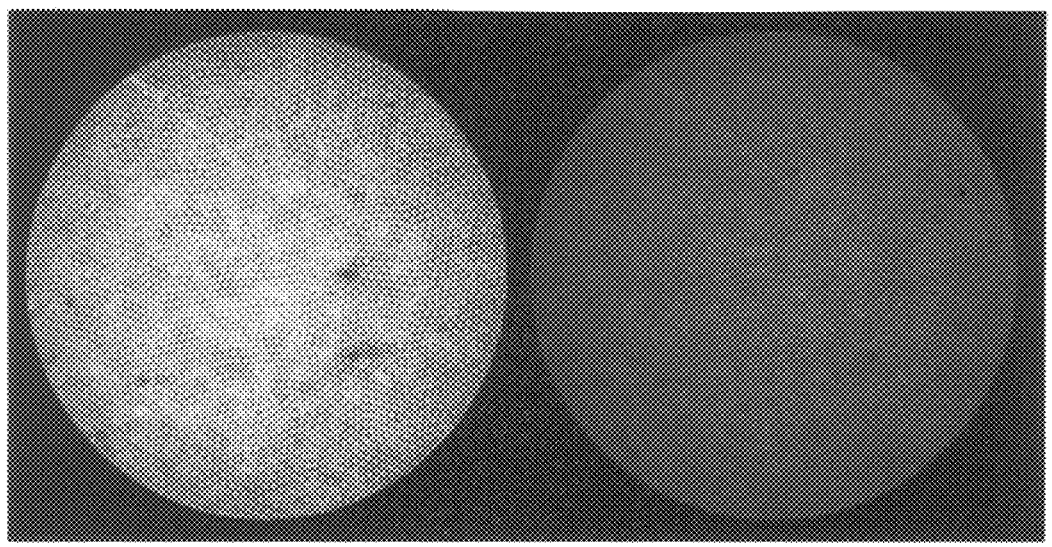
FIG. 19: RBITC fluorescence images acquired from the same RBITC-IFCP immersed in PBS (left) and 0.25 mM $H_2O_2$/PBS (right). The CCD exposure time was 1 s; white represents high fluorescence intensities (both images were normalized to the same grayscale).

An example of a possible mechanism of operation for RBITC-IFECS fluorescence imaging is shown in FIG. 15. In brief, as hydrogen peroxide diffuses into the NAFION layer, it is oxidized by the RBITC immobilized in the NAFION layer. This homogeneous electron transfer reaction decreases the RBITC concentration and the RBITC fluorescence at the IFECS surface in proportion to the $H_2O_2$ concentration. To evaluate this aspect of the proposed mechanism, NAFION-modified imaging fibers were used to fabricate RBITC-IFCPs. FIG. 19 shows a representative RBITC fluorescence image captured through a RBITC-IFCP submerged in PBS and through the same RBITC-IFCP submerged in 0.25 mM $H_2O_2$/PBS. In brief, the mean RBITC fluorescence intensity decreased ~45% upon $H_2O_2$ exposure (n>20 IFCPs tested). As predicted by the RBITC-IFECS mechanism of operation (FIG. 15), when RBITC-IFCPs that had been exposed to $H_2O_2$ were re-immersed in PBS (without $H_2O_2$) the mean fluorescence intensity did not return to initial values (n>10 IFCPs tested). Additionally, it should be noted that RBITC fluorescence intensities did not change when RBITC-IFCPs were immersed in $H_2O_2$ solutions whose pH was in the pH 6–8 range or whose oxygen partial pressure was in the 200–600 torr range. Not surprisingly, the ~45% intensity decrease was identical to that captured through a polished imaging fiber's distal face that was immersed first in 0.25 mM RBITC/PBS and then in 0.25 mM $H_2O_2$+0.25 mM RBITC/PBS (n>15 mixtures tested).

Figure 18:
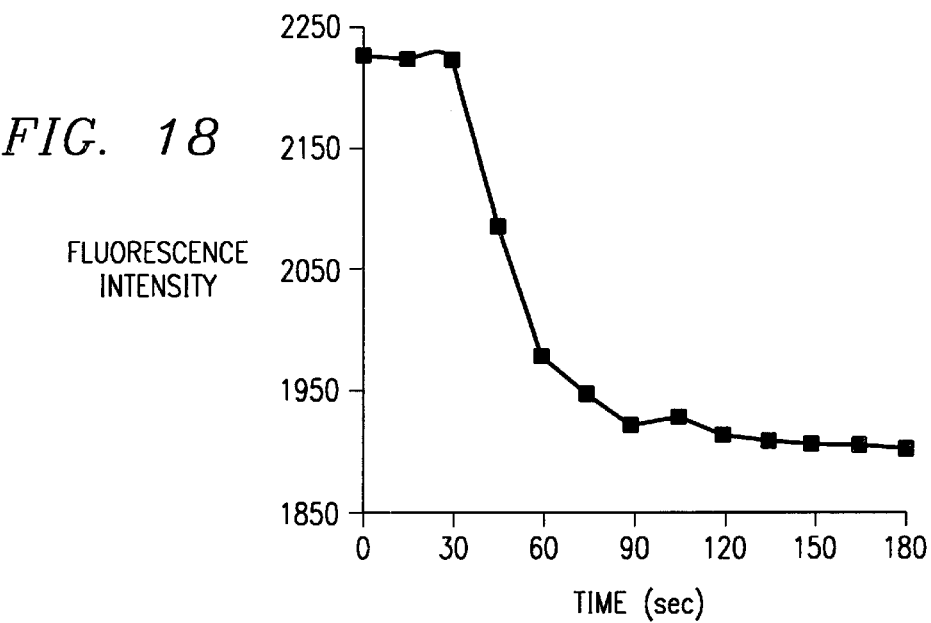
FIG. 18: Mean RBITC fluorescence from a RBITC-IFCP as a function of time before (i.e., the first 3 data points) and after the manual injection of 0.25 mM $H_2O_2$. All measurements were acquired with a 2-s CCD acquisition time at 15-s intervals.

The temporal response of RBITC-IFCPs were characterized by capturing fluorescence images before and after the manual pipette injection of a 1-mL aliquot of $H_2O_2$ to the distal tip of a RBITC-IFCP submerged in a ~10-microliter drop of PBS (FIG. 18). The RC-time constant (defined as the time required to reach 63% of the maximum response) of the RBITC-IFCP to 0.25 mm $H_2O_2$ was ~24 s (n=4 IFCPs tested). Faster response times were observed as the $H_2O_2$ concentration was decreased indicating that mass transport into the polymer layer was the rate-limiting step as shown in studies conducted in part by one of the present inventors [Bronk, K. S., Michael, K. L., Pantano, P. & Walt, D. R. (1995) Anal. Chem. 67:2750].

Figure 20:
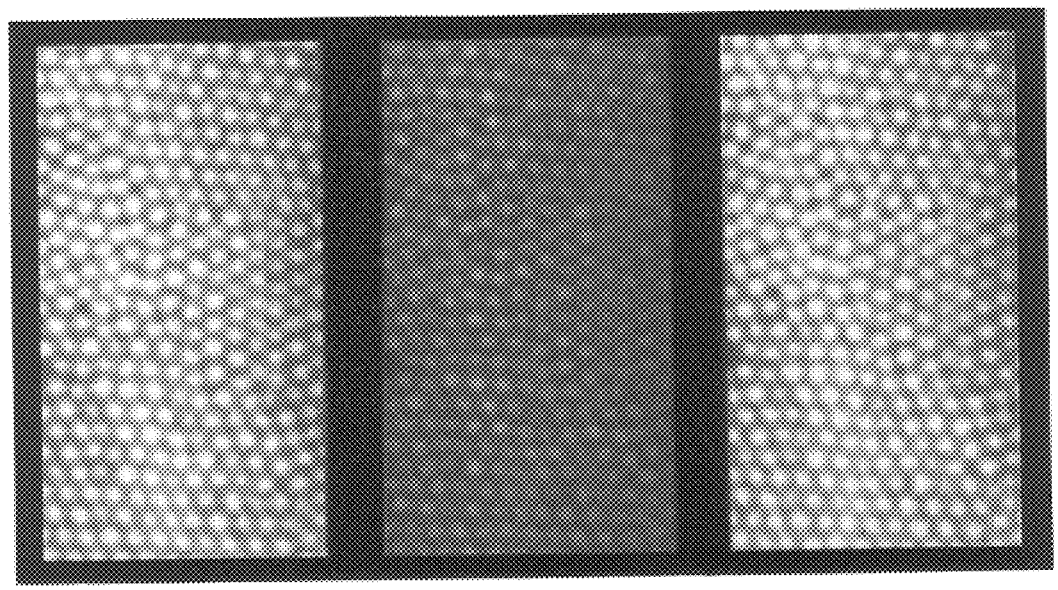
FIG. 20: RBITC fluorescence images acquired from the same RBITC-IFECS immersed in: PBS (left), 0.25 mM $H_2O_2$/PBS (middle), and PBS after application of a 30-min, −600 mV DC potential (right). The CCD exposure time was 5 s; white represents high fluorescence intensities (all three images were normalized to the same grayscale).

The present invention in one example provides reversible IFECS in which the NAFION-immobilized RBITC can be regenerated. The RBITC cyclic voltammograms shown in FIG. 17 indicate that the application of −600 mV DC potential across the IFECS should oxidize the reduced-form of RBITC. FIG. 20-left shows a representative RBITC fluorescence image captured through a RBITC-IFECS submerged in PBS. FIG. 20-middle shows a representative RBITC fluorescence image when the RBITC-IFECS was submerged in 0.25 mM $H_2O_2$/PBS. In brief, the mean RBITC fluorescence intensity decreased ~27% upon $H_2O_2$ exposure. When this RBITC-IFECS was immersed again in PBS (without $H_2O_2$) the mean fluorescence intensity did not change (data not shown but identical to that observed with RBITC-IFCPs). FIG. 20-right shows the RBITC fluorescence image when the RBITC-IFECS was submerged in PBS following the 30-min application of a −600 mV potential. The increase in the mean fluorescence intensity following the applied potential (FIG. 20-right) was significant; specifically, 95% of the original RBITC-IFECS fluorescence (FIG. 20-left) was observed (n=9 IFECSs tested using $H_2O_2$ concentrations between 5 $\mu$M to 5 mM) indicating that immobilized RBITC was electrochemically regenerated.

While ROS and oxidative stress (i.e., a relative overload of ROS) have been implicated in the pathophysiology of a large number of diseases, to date, there are no remote ROS-imaging sensors that have the size, speed and selectivity required for dynamic measurements of in situ biochemical processes. In this example, one aspect of the invention provides a stable imaging-fiber electrode surface upon which reversible voltammetry and optical imaging can be performed, and its use to form an electrochemically-modulated, fluorescence-based imaging-fiber electrode chemical sensor (IFECS). The use of IFECSs to image electroactive ROS provides a new and powerful tool in investigating the biological role of ROS at the level of a single cell. For example, the IFECSs of the present example may be applied for use with single cells since they can reduce the precision with which an extremely small probe must be positioned (e.g., a 1-mm diameter, high resolution imaging fiber (with individual core diameters on the order of ~3 micrometer), would be able to simultaneously image ~150 fibroblasts). IFECSs also possess the novel capability of permitting simultaneous fluorescence and electrochemical detection to be performed in order to increase the selectivity of the analytical measurement.

Reagents and Materials

Rhodamine B isothiocyanate (RBITC), 95% (3-mercaptopropyl)-trimethoxysilane (MPS), tris(2,2'-bipyridyl)ruthenium(II) chloride hexahydrate ($Ru(bpy)_3^{2+}$), and NAFION were purchased from Aldrich Chemical Co. (Milwaukee, Wis.). MPS solutions were prepared by adding 1 g MPS to a mixture of 1 g deionized water and 40 g isopropyl alcohol. Phosphate buffer solution (PBS; 137 mM NaCl, 2.7 mM KCl, and 10 mM phosphate, pH 7.4 at 25° C.) was prepared using phosphate buffer tablets obtained from Fluka Chemical Co. (Ronkonkoma, N.Y.). Piranha solutions were prepared by mixing 30% hydrogen peroxide and concentrated sulfuric acid in a 1:4 volumetric ratio. All chemicals were used as received without further purification; chemicals not listed were of reagent grade. Deionized water (18 megaohm-cm) was obtained using a Nanopure Infinity water purification system (Barnstead, Dubuque, Iowa).

Silica imaging fibers (3–20 ft long) with a total diameter of ~350 micrometer comprising ~6000 individually-cladded ~3-micrometer diameter optical fibers were purchased from Sumitomo Electric Industries (Part No. IGN-035/06; Torrance, Calif.). The active imaging diameter of the coherent fiber optic bundle was ~270 micrometer (i.e., the individual optical fibers were fused within a ~15-micrometer thick silica tube and this tube was coated with a ~25-micrometer thick silicone jacket).

Imaging Fiber Chemical Probe (IFCP) Fabrication

RBITC-IFCP fabrication began with securing an imaging fiber in an appropriate fiber chuck (General Fiber Optics, Fairfield, N.J.) and successively polishing each fiber face with 12-, 3-, 1-, and 0.3-micrometer lapping films (Mark V Laboratory, East Granby, Conn.). Polished fiber tips were sonicated in deionized water for 30 s to remove any lapping film residuals and fiber particulates. Distal fiber faces were cleaned chemically by soaking them in Piranha solution at 70° C. for 20 min. Following a deionized water rinse, the entire fiber was dried in air at 23° C. for 5 min and in an oven at 105° C. for 10 min.

NAFION spin coating was performed with a Servodyne mixer/spinner comprising an inverted mixer-head and a digital RPM controller (Cole-Parmer Instrument Co., Veron Hills, Ill.). The polished imaging fiber was mounted vertically onto the spinner mixer-head. A 20-microliter NAFION aliquot was dispensed onto the distal fiber face and the fiber was spun at 2000 RPM for 1 min. The Nafion layer was dried in air at room temperature for 15 min and the process was repeated. NAFION-modified imaging fibers were dried in air at room temperature for 2–3 h before further processing. NAFION-modified imaging fibers were soaked in a 0.25 mM RBITC/PBS for 2 h, and the resulting RBITC-IFCPs were rinsed with PBS to remove non-immobilized dye.

Imaging Fiber Electrode (IFE) Fabrication

IFE fabrication started with removing the distal-most ~1-inch of the imaging fiber's silicone resin coating using acetone. The distal and proximal faces were polished as described above. To enhance gold film adhesion to an imaging fiber's silica surface, the polished fiber's distal end was MPS silanized according to the method of Goss, C. A. et al., (1991) *Anal. Chem.* 63:85. The cleaned and dried fiber's distal tip was immersed in refluxing MPS for 10 min, and the fiber was rinsed gently with isopropyl alcohol. The fiber was dried in air at 23° C. for 1 min and in an oven at 105° C. for 8 min. The MPS immersion, rinsing, and drying process was performed three times.

The final IFE fabrication step was the deposition of a semi-transparent gold layer onto an MPS-silanized imaging fiber distal tip. A Hummer model VII sputtering coater (Anatech Ltd., Springfield, Va.) with a solid gold sputtering target was used for gold film deposition on imaging fiber distal tips. MPS-silanized, imaging fiber distal tips were mounted normal to the sputter coater's chamber platform facing the solid gold target. The sample chamber was evacuated to 40 mtorr and argon gas was introduced into the chamber to bring the pressure to 80 mtorr. The imaging fiber distal tips were gold coated at a 4-nm/min rate; the desired film thickness was ~20 nm as estimated by transmitted light intensity monitoring using a model 1815-C optical power meter with an 818-UV series photodetector (Newport Co., Irvine, Calif.).

Imaging Fiber Electrode Chemical Sensor (IFECS) Fabrication

An IFE was NAFION spin-coated as described above and the NAFION-modified IFE was soaked in 0.25 mM RBITC/PBS for 2 h. The resulting RBITC-IFECS was rinsed with PBS to remove non-immobilized dye. The resulting configuration of the RBITC-IFECS is depicted in FIG. 14.

RBITC Fluorescence Imaging

Fluorescence imaging was performed with a modified epi-fluorescence microscope (Labophot 1A; Nikon, Irving, Tex.) similar to the one described by Bronk, K. S., Michael, K. L., Pantano P. & Walt, D. R.(1995) *Anal. Chem.* 67:2750.

In brief, collimated excitation radiation from a 75-W xenon-arc lamp was passed through a neutral density filter(s) to control the excitation intensity. The radiation was passed through a 500±40 nm excitation filter (Omega Optical, Brattleboro, Vt.), was reflected 90° by a 560-nm dichroic mirror, and focused through a 10× E-Plan microscope objective onto the imaging fiber's proximal face. The light was transmitted through the imaging fiber to the fiber's distal face where it excited immobilized RBITC. The returning fluorescence was transmitted through the same fiber and collected by the same microscope objective. The fluorescence was passed through the dichroic mirror and filtered by a 580±15 nm emission filter. The fluorescence image was captured by a charge coupled device (CCD) camera. The 512×768 pixel, 1-MHZ, 12-bit, −15° C. cooled, MicroMax CCD camera was purchased from Princeton Instruments (Trenton, N.J.). WinView image-processing software (Princeton Instruments) and a Pentium-II PC were used to control CCD functions and to collect and process all images. In general, a 250×250 region of interest (ROI) was selected from the image of a RBITC-IFCP or RBITC-IFECS's sensing layer and the ROI's mean fluorescence intensity was used for quantitation purposes.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A sensor probe for detecting an analyte comprising:
    a fiber optic layer;
    an electrically conductive translucent metallic layer disposed on the fiber optic layer; and
    a light energy absorbing dye disposed on the metallic layer.

2. The sensor probe of claim 1, wherein the fiber optic layer comprises a fiber optic bundle.

3. The sensor probe of claim 1 wherein the electrically conductive translucent metallic layer is between 10 and 100 nm thick.

4. The sensor probe of claim 1 wherein the electrically conductive translucent metallic layer is between 15 and 30 nm thick.

5. The sensor probe of claim 1 wherein the electrically conductive translucent metallic layer comprises a layer of gold between 10 and 30 nm thick.

6. The sensor probe of claim 1 wherein the light energy absorbing dye is selected from the group consisting of fluorochromes, fluorescent enzyme conjugates, fluorescent substrates and chromophores.

7. The sensor probe of claim 1 wherein the analyte is a cellular reactive oxygen species and the light energy absorbing dye comprises a rhodamine dye.

8. The sensor probe of claim 1 wherein the analyte is a cellular NADH and the light energy absorbing dye comprises a ruthenium containing luminophore.

9. A fiber optic electrochemical sensor for detecting an analyte comprising:
    a fiber optic bundle having a first and a second end;
    an electrically conductive translucent metallic layer disposed on the first end of the fiber optic bundle; and
    a light energy absorbing dye layer disposed on the metallic layer.

10. The fiber optic electrochemical sensor of claim 9 wherein individual fibers of the fiber optic bundle comprise a diameter of less than 20 micrometers.

11. The fiber optic electrochemical sensor of claim 9 wherein the electrically conductive translucent metallic layer is between 10 and 100 nm thick.

12. The fiber optic electrochemical sensor of claim 9 wherein the electrically conductive translucent metallic layer is between 15 and 30 nm thick.

13. The fiber optic electrochemical sensor of claim 9 wherein the electrically conductive translucent metallic layer comprises a layer of gold between 10 and 30 nm thick.

14. The fiber optic electrochemical sensor of claim 9 wherein the light energy absorbing dye layer is selected from the group consisting of fluorochromes, fluorescent enzyme conjugates, fluorescent substrates and chromophores.

15. The fiber optic electrochemical sensor of claim 9 wherein the analyte is a cellular reactive oxygen species and the light energy absorbing dye layer comprises a rhodamine dye.

16. The fiber optic electrochemical sensor of claim 9 wherein the analyte is a cellular NADH and the light energy absorbing dye layer comprises a ruthenium containing luminophore.

17. A fiber optic electrochemical sensor for detecting an analyte comprising:
    a fiber optic bundle comprised of individual optic fibers wherein each individual optic fiber has a diameter of less than 10 micrometers and wherein the bundle has a diameter of less than 2 millimeters having first and second ends;
    an electrically conductive translucent metallic layer disposed on the first end of the fiber optic bundle; and
    a light energy absorbing dye layer disposed on the metallic layer,
    wherein the fiber optic electrochemical sensor is capable of electrochemical regeneration of the light absorbing dye layer.

18. A fluorescence based imaging fiber electrode chemical sensor system comprising:
    a fiber optic electrochemical sensor;
    a potentiomer in electric communication with the fiber optic electrochemical sensor;
    a microscope including a light source and an objective in optic communication with the fiber optic electrochemical sensor wherein the objective communicates light from the source to the fiber optic electrochemical sensor and receives light returning from the sensor; and
    a means for recording light returning from the sensor though the objective.

19. A method for preparing a imaging fiber electrode comprising the steps of:
    polishing a face of the fiber optic bundle;
    silanizing the face using a trimethyoxysilane; and
    sputter coating the silanized face to deposit a 10–30 nm thick semi-transparent metal layer.

20. A method for preparing a imaging fiber chemical sensor comprising the steps of:
    obtaining a fiber optic electrode having a 15–30 nm gold film on a distal end and an electrically conductive aspect leading from the distal end and along a lateral dimension of the fiber optic electrode;
    coating the fiber optic electrode with an ion-exchange polymer; and
    applying a luminescent reporter group.

21. The method of claim 20 wherein the ion-exchange polymer is a poly(tetrafluorethylene) polymer having characteristics of a NAFION polymer.

22. The fiber optic electrochemical sensor for detecting an analyte of claim 20 wherein:

the fiber optic layer comprises a fiber optic array comprising a plurality of optical fibers wherein each optical fiber has a diameter of less than 10 micrometers and wherein the array is dimensioned for microscopic resolution;

the electrically conductive translucent metallic layer comprises an essentially thin uniform gold film disposed across a distal face of the fiber optic array wherein the film is semi-transparent to light and is electrically conductive;

the light energy absorbing dye layer is reactive with an analyte of interest wherein the reaction with the analyte results directly or indirectly in light emission transmittable along the fiber optic array; and further comprising:

an electrically conductive conveyance disposed co-axially along the length of the fiber optic array from the gold film to a device for recording a electric signal emanating from the gold film.

* * * * *